US008111286B2

(12) United States Patent
Inuiya et al.

(10) Patent No.: US 8,111,286 B2
(45) Date of Patent: Feb. 7, 2012

(54) IMAGE PROCESSING APPARATUS, ENDOSCOPE, AND COMPUTER READABLE MEDIUM

(75) Inventors: Masafumi Inuiya, Kanagawa (JP); Yuichi Ohashi, Tokyo (JP); Mikio Ihama, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 1166 days.

(21) Appl. No.: 11/863,651

(22) Filed: Sep. 28, 2007

(65) Prior Publication Data
US 2008/0079807 A1    Apr. 3, 2008

(30) Foreign Application Priority Data

Sep. 28, 2006 (JP) ................. 2006-264923
Sep. 28, 2006 (JP) ................. 2006-264926

(51) Int. Cl.
*A61B 1/06* (2006.01)
*H04N 5/33* (2006.01)
(52) U.S. Cl. .......................... 348/70; 348/164
(58) Field of Classification Search ............. 348/70
See application file for complete search history.

(56) References Cited

U.S. PATENT DOCUMENTS

| 5,550,582 | A | 8/1996 | Takasugi et al. |
| 5,675,378 | A | 10/1997 | Takasugi et al. |
| 2003/0187319 | A1* | 10/2003 | Kaneko et al. ............ 600/9 |
| 2005/0029456 | A1* | 2/2005 | Eggers et al. ......... 250/339.02 |
| 2005/0225656 | A1 | 10/2005 | Ihama |
| 2006/0081887 | A1 | 4/2006 | Lyu |
| 2006/0084195 | A1 | 4/2006 | Lyu |
| 2006/0119724 | A1 | 6/2006 | Inuiya |
| 2006/0196533 | A1 | 9/2006 | Maehara |
| 2006/0211915 | A1 | 9/2006 | Takeuchi et al. |
| 2008/0153193 | A1 | 6/2008 | Lyu |

FOREIGN PATENT DOCUMENTS

| JP | 06-204445 A | 7/1994 |
| JP | 6-335451 A | 12/1994 |
| JP | 2648494 B2 | 5/1997 |
| JP | 2002-521975 A | 7/2002 |
| JP | 2004-080565 A | 3/2004 |
| JP | 2005-006066 A | 1/2005 |
| JP | 2005-065976 A | 3/2005 |
| JP | 2005-302806 A | 10/2005 |

(Continued)

OTHER PUBLICATIONS

Japanese Office Action issued in Application No. 2006-264926, dated Mar. 8, 2011.

(Continued)

*Primary Examiner* — Firmin Backer
*Assistant Examiner* — Herman Belcher
(74) *Attorney, Agent, or Firm* — Sughrue Mion, PLLC

(57) ABSTRACT

An image processing apparatus includes a color image data generation section 54 that generates color image data from an image pickup signal of a red component, an image pickup signal of a green component, and an image pickup signal of a blue component which are output from an image pickup device 100; an infrared image data generation section 53 that generates infrared image data from an image pickup signal of an infrared component output from the image pickup device 100; and a high-contrast infrared image data generation section 55 that generates high-contrast infrared image data using the color image data and the infrared image data. Contrast of the high-contrast infrared image data is more enhanced than that of the infrared image data.

21 Claims, 18 Drawing Sheets

FOREIGN PATENT DOCUMENTS

| | | |
|---|---|---|
| JP | 2005-341470 A | 12/2005 |
| JP | 2006-121093 A | 5/2006 |
| JP | 2006-165663 A | 6/2006 |
| JP | 2006-239206 A | 9/2006 |
| JP | 2006-245045 A | 9/2006 |
| WO | 00/07365 A1 | 2/2000 |

OTHER PUBLICATIONS

Japanese Office Action, dated Aug. 23, 2011, issued in Japanese Application No. 2006-264923.

\* cited by examiner

- - - - - : PHOTOELECTRIC CONVERSION LAYER 9
———— : TRANSMISSIVITY OF PHOTOELECTRIC CONVERSION LAYER 9
········· : PD

----------- : R FIRST PHOTOELECTRIC CONVERSION ELEMENT
— — — — : G FIRST PHOTOELECTRIC CONVERSION ELEMENT
——————— : B FIRST PHOTOELECTRIC CONVERSION ELEMENT
—·—·—· : R SECOND PHOTOELECTRIC CONVERSION ELEMENT
········· : G SECOND PHOTOELECTRIC CONVERSION ELEMENT
——————— : B SECOND PHOTOELECTRIC CONVERSION ELEMENT

FIG. 13
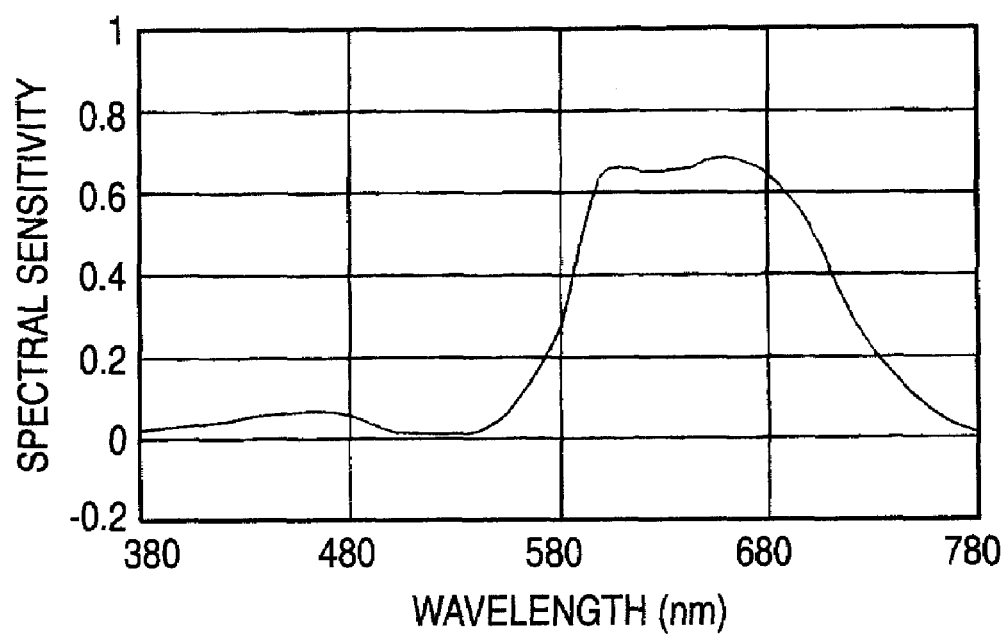
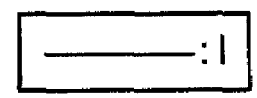

FIG. 14
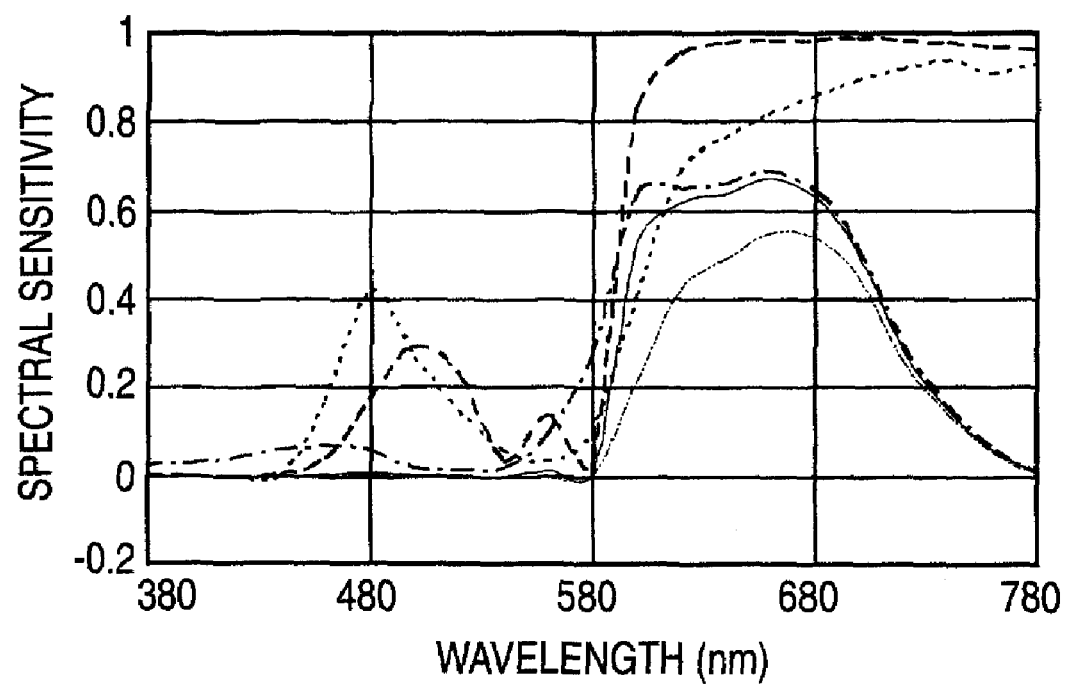
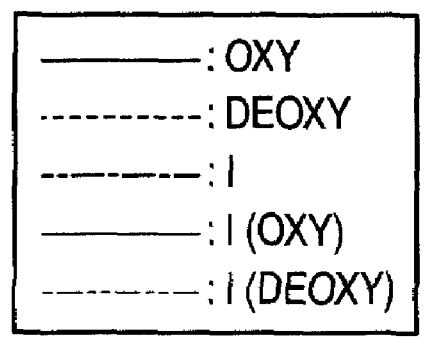

FIG. 16
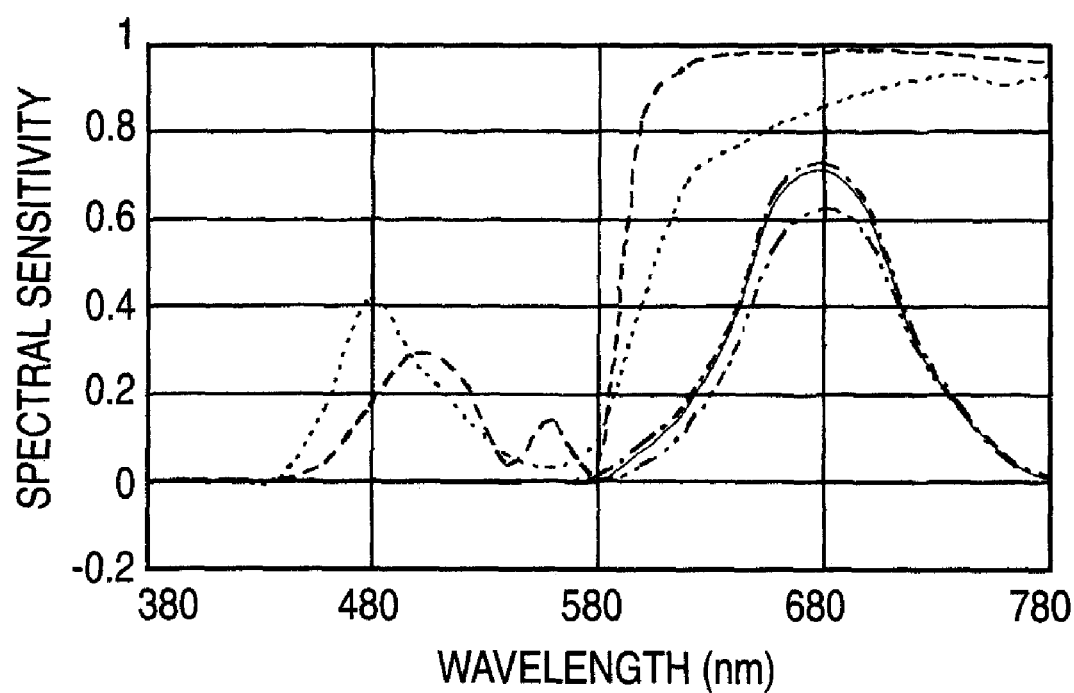
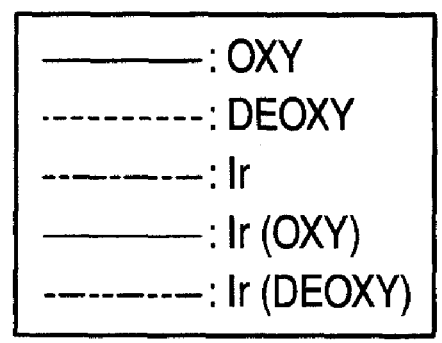

IMAGE PROCESSING APPARATUS, ENDOSCOPE, AND COMPUTER READABLE MEDIUM

CROSS-REFERENCE TO RELATED APPLICATIONS

This application is based upon and claims the benefit of priority from the Japanese Patent Application Nos. 2006-264923 (filed on Sep. 28, 2006) and 2006-264926 (filed on Sep. 28, 2006), the entire contents of which are incorporated herein by reference.

BACKGROUND OF THE INVENTION

1. Technical Field

This invention relates to an image processing apparatus for performing image processing for an image pickup signal output from an image pickup device, an endoscope and a computer readable medium storing an image processing program.

2. Description of the Related Art

An endoscope using a CCD or CMOS image sensor as an image pickup device is already often used in the medical field. The endoscopes are roughly classified into (i) a frame sequential image pickup method of using an image pickup device capable of picking up a monochrome image and switching a filter for transmitting light of wavelength ranges of R (red), G (green), B (blue), and IR (infrared) in front of a light source for illuminating a subject through a fiber in synchronization with the field frequency of the image pickup device (for example, see Japanese Patent No. 2648494) and (ii) a simultaneous image pickup method of picking up an image using a single-plate image pickup device provided with a color filter for transmitting light of wavelength ranges of R, G, and B and an illumination light source that emits white light.

The frame sequential image pickup method is a method of rotating a plurality of filters having different spectral transmissivitys in front of a light source and picking up a plurality of images illuminated by light of different wavelengths and then combining the images into a color image. Thus, for example, if RGB transmission filters are used as the filters switched in front of the light source, color image data having three color information pieces of RGB in one pixel data can be provided. Also, if IR filters of two wavelengths put into a narrow band easily absorbed by hemoglobin in blood are switched in sequence, infrared image data in which one pixel data only has information of an infrared region can be provided. An image based on the color image data enables a user to visually check an appearance of a part to be tested, and an image based on the infrared image data enables the user to visually check information, etc., of blood capillary of mucosal surface layer and a mucosal minute pattern in the part to be tested. However, in the frame sequential image pickup, a color shift occurs for a subject involving motion, resulting in image interference.

On the other hand, the simultaneous image pickup method is a method of obtaining color image data by picking up an image and then performing image processing for the color image data, thereby generating infrared image data. According to this method, a color shift does not occur for a subject involving motion, but there is a problem of low information accuracy of the infrared image data.

Thus, an image pickup device used with an endoscope can obtain color image data in which one pixel has three-color (RGB) information and infrared image data in which one pixel only has infrared information by the apparatus configuration disclosed in Japanese Patent No. 2648494 or the image processing. Particularly, the infrared image data is used to check information, etc., of blood capillary of mucosal surface layer and a mucosal minute pattern in the part to be tested. Therefore, high contrast is demanded for the infrared image data.

Also, color reproducibility of the RGB color image data will be described. Usually, R, G, and B color filters also transmit infrared-region wavelength. Thus, if light passing through the R, G, and B color filters is detected in the photoelectric conversion elements and RGB color image data is generated, the color reproducibility thereof is not good. Then, an infrared (IR) cut filter is provided in front of an image pickup device using R, G, and B color filters so that the light passing through the R, G, and B color filters does not contain infrared-region light. Thereby, the color reproducibility is improved.

However, an IR cut filter having a steep IR cut property is expensive and is at high cost. An IR cut filter must be provided in front of the image pickup device and miniaturization of whole system using the image pickup device is also hindered. If an attempt is made to use an IR cut filter in the apparatus described in Japanese Patent No. 2648494, only when R, G, and B color filters come in front of the image pickup device, the IR cut filter needs to be placed in front of the R, G or B filter, and the mechanism and control of the system become complicated.

SUMMARY OF THE INVENTION

The invention provides an image processing apparatus capable of generating infrared image data with high contrast from an image pickup signal obtained from an image pickup device.

Also, the invention may further provide an image processing apparatus capable of generating RGB color image data good in color reproducibility from the image pickup signal from the image pickup device without providing an IR cut filter in front of the image pickup device.

(1) According to an aspect of the invention, an image processing apparatus for generating image data from an image pickup signal output from an image pickup device includes a color image data generation unit, an infrared image data generation unit and a high-contrast infrared image data generation unit. The color image data generation unit generates color image data from an image pickup signal of a red component, an image pickup signal of a green component, and an image pickup signal of a blue component which are output from the image pickup device. The infrared image data generation unit generates infrared image data from an image pickup signal of an infrared component output from the image pickup device. The high-contrast infrared image data generation unit generates high-contrast infrared image data using the color image data and the infrared image data. Contrast of the high-contrast infrared image data is more enhanced than that of the infrared image data.

(2) In the image processing apparatus of (1), pixel data of the color image data may include red-component data, green-component data and blue-component data. Pixel data of the infrared image data may include infrared-component data. The high-contrast infrared image data generation unit may generate the high-contrast infrared image data using the following expression:

$$I(x,y) = r1 \times R(x,y) + g1 \times G(x,y) + b1 \times B(x,y) + ir1 \times IR(x,y)$$

where I(x, y) denotes pixel data of the high-contrast infrared image data at coordinates (x, y), R(x, y) denotes the red-component data of the pixel data at the coordinates (x, y), G(x, y) denotes the green-component data of the pixel data at the coordinates (x, y), B(x, y) denotes the blue-component data of the pixel data at the coordinates (x, y), and r1, g1, b1 and ir1 denote coefficients. The coefficients r1, g1, b1, and ir1 are determined so that r1×R(λ)+g1×G(λ)+b1×B(λ)+ir1×IR(λ) is as close as possible to Real(λ), where R(λ) denotes a spectral sensitivity of a red-component photoelectric conversion element of the photoelectric conversion elements that outputs the image pickup signal of the red component, G(λ) denotes a spectral sensitivity of a green-component photoelectric conversion element of the photoelectric conversion elements that outputs the image pickup signal of the green component, B(λ) denotes a spectral sensitivity of a blue-component photoelectric conversion element of the photoelectric conversion elements that outputs the image pickup signal of the blue component, IR(λ) denotes a spectral sensitivity of an infrared-component photoelectric conversion element of the photoelectric conversion elements that outputs the image pickup signal of the infrared component, and Real(λ) denotes a spectral sensitivity with which a observation target substance used to grasp change in a human body can be picked up with the highest contrast (3) In the image processing apparatus of (2), the observation target substance may be hemoglobin.

(4) The image processing apparatus of any one of (1) to (3) may further include a high-color-reproduction color image data generation unit. The high-color-reproduction color image data generation unit generates high-color-reproduction color image data using the color image data and the infrared image data. The high-color-reproduction color image data has color reproducibility higher than the color image data.

(5) In the image processing apparatus of (4), the high-color-reproduction color image data generation unit may generate each pixel data of the high-color-reproduction color image data using the following expression:

$$\begin{pmatrix} R_O(x, y) \\ G_O(x, y) \\ B_O(x, y) \end{pmatrix} = \begin{pmatrix} r2 & g2 & b2 & ir2 \\ r3 & g3 & b3 & ir3 \\ r4 & g4 & b4 & ir4 \end{pmatrix} \begin{pmatrix} R(x, y) \\ G(x, y) \\ B(x, y) \\ Ir(x, y) \end{pmatrix}$$

where $R_O(x, y)$ denotes red-component data of the pixel data of the high-color-reproduction color image data at coordinates (x, y), $G_O(x, y)$ denotes green-component data of the pixel data of the high-color-reproduction color image data at the coordinates (x, y), $B_O(x, y)$ denotes blue-component data of the pixel data of the high-color-reproduction color image data at the coordinates (x, y), R(x, y) denotes the red-component data of the pixel data of the color image data at the coordinates (x, y), G(x, y) denotes the green-component data of the pixel data of the color image data at the coordinates (x, y), B(x, y) denotes the blue-component data of the pixel data of the color image data at the coordinates (x, y), Ir(x, y) denotes the infrared-component data of the pixel data of the color image data at the coordinates (x, y), and r2, r3, r4, g2, g3, g4, b2, b3, b4, ir2, ir3 and ir4 denote coefficients. The coefficients r2, g2, b2, and ir2 are determined so that r2×R(λ)+g2×G(λ)+b2×B(λ)+ir2×IR(λ) is as close as possible to $R_O(λ)$, where R(λ) denotes a spectral sensitivity of a red-component photoelectric conversion element of the photoelectric conversion elements that outputs the image pickup signal of the red component, G(λ) denotes a spectral sensitivity of a green-component photoelectric conversion element of the photoelectric conversion elements that outputs the image pickup signal of the green component, B(λ) denotes a spectral sensitivity of a blue-component photoelectric conversion element of the photoelectric conversion elements that outputs the image pickup signal of the blue component, IR(λ) denotes a spectral sensitivity of an infrared-component photoelectric conversion element of the photoelectric conversion elements that outputs the image pickup signal of the infrared component, and $R_O(λ)$ denotes an ideal spectral sensitivity of a photoelectric conversion element that outputs an image pickup signal of the red component. The coefficients r3, g3, b3, and ir3 are determined so that r3×R(λ)+g3×G(λ)+b3×B(λ)+ir3×IR(λ) is as close as possible to $G_O(λ)$, where $G_O(λ)$ denotes an ideal spectral sensitivity of a photoelectric conversion element that outputs an image pickup signal of the green component. The coefficients r4, g4, b4, and ir4 are determined so that r4×R(λ)+g4×G(λ)+b4×B(λ)+ir4×IR(λ) is as close as possible to $B_O(λ)$, where $G_O(λ)$ denotes an ideal spectral sensitivity of a photoelectric conversion element that outputs an image pickup signal of the blue component.

(6) In the image processing apparatus of any one of (1) to (5), wherein the image pickup device may include a large number of first photoelectric conversion elements, second photoelectric conversion elements, a color filter layer and a signal reading portion. The first photoelectric conversion elements are arranged on a first plane in a semiconductor substrate. The second photoelectric conversion elements are formed on a second plane, which is located above the first photoelectric conversion elements. The second photoelectric conversion elements correspond to a part of the large number of first photoelectric conversion elements. The second photoelectric conversion elements include first electrodes formed above the first photoelectric conversion elements. The photoelectric conversion layer is formed on the first electrodes, and a second electrode formed on the photoelectric conversion layer. The color filter layer is formed above the first photoelectric conversion elements. The color filter layer transmits light in a wavelength range different from a wavelength range of light that the photoelectric conversion layer absorbs. The signal reading portion reads (i) signals that correspond to charges generated in the second photoelectric conversion elements and (ii) signals that correspond to charges generated in the first photoelectric conversion elements. The color filter layer include a large number of color filters that correspond to the large number of photoelectric conversion elements, respectively. The large number of color filters are classified into three types of color filters of those for transmitting light in a red wavelength range, those for transmitting light in a green wavelength range, and those for transmitting light in a blue wavelength range. Of the three types of color filters, at least the color filters for transmitting light in the red wavelength range also transmit infrared region light. The photoelectric conversion layer absorbs the infrared region light to generate charges in response thereto, and transmits any other light than the infrared region light. The part of the large number of first photoelectric conversion elements are the first photoelectric conversion elements corresponding to the color filters for transmitting light in the red wavelength range.

(7) In the image processing apparatus of (6), the color filter layer may be formed above the second photoelectric conversion elements.

(8) In the image processing apparatus of (7), the photoelectric conversion layer may contain an organic material. The image pickup device may further include a protective layer that protects the second photoelectric conversion elements. The protective layer is formed by an ALCVD method between the first photoelectric conversion elements and the color filter layer.

(9) In the image processing apparatus of (8), the protective layer may contain an inorganic material.

(10) In the image processing apparatus of (9), the protective layer may have a two-layer structure including an inorganic layer made of an inorganic material and an organic layer made of an organic polymer.

(11) In the image processing apparatus of any one of (6) to (10), the image pickup device may further include a microlens that collects light in each of the large number of first photoelectric conversion elements.

(12) According to another aspect of the invention, an endoscope includes an image processing apparatus; and the image processing apparatus of any one of (1) to (11).

(13) According to further another aspect of the invention, a computer readable medium stores a program for causing a computer to execute a process for image processing. The image processing includes: generating color image data from an image pickup signal of a red component, an image pickup signal of a green component, and an image pickup signal of a blue component which are output from an image pickup device; generating infrared image data from an image pickup signal of an infrared component output from the image pickup device; and generating high-contrast infrared image data using the color image data and the infrared image data. Contrast of the high-contrast infrared image data is more enhanced than that of the infrared image data.

According to any of the above configurations of (1) to (13), there can be provided an image processing apparatus capable of generating infrared image data in high contrast from an image pickup signal obtained from an image pickup device, an endoscope and a computer readable medium storing an image processing program.

(14) According to still further another aspect of the invention, an image processing apparatus for generating image data from an image pickup signal output from an image pickup device includes a color image data generation unit, an infrared image data generation unit and a high-color-reproduction color image data generation unit. The color image data generation unit generates color image data from an image pickup signal of a red component, an image pickup signal of a green component, and an image pickup signal of a blue component which are output from the image pickup device. The infrared image data generation unit generates infrared image data from an image pickup signal of an infrared component output from the image pickup device. The high-color-reproduction color image data generation unit generates high-color-reproduction color image data using the color image data and the infrared image data. The high-color-reproduction color image data has color reproducibility higher than the color image data.

(15) In the image processing apparatus of (14), the high-color-reproduction color image data generation unit may generate each pixel data of the high-color-reproduction color image data using the following expression:

$$\begin{pmatrix} R_O(x, y) \\ G_O(x, y) \\ B_O(x, y) \end{pmatrix} = \begin{pmatrix} r2 & g2 & b2 & ir2 \\ r3 & g3 & b3 & ir3 \\ r4 & g4 & b4 & ir4 \end{pmatrix} \begin{pmatrix} R(x, y) \\ G(x, y) \\ B(x, y) \\ Ir(x, y) \end{pmatrix}$$

where $R_O(x, y)$ denotes red-component data of the pixel data of the high-color-reproduction color image data at coordinates (x, y), $G_O(x, y)$ denotes green-component data of the pixel data of the high-color-reproduction color image data at the coordinates (x, y), $B_O(x, y)$ denotes blue-component data of the pixel data of the high-color-reproduction color image data at the coordinates (x, y), R(x, y) denotes the red-component data of the pixel data of the color image data at the coordinates (x, y), G(x, y) denotes the green-component data of the pixel data of the color image data at the coordinates (x, y), B(x, y) denotes the blue-component data of the pixel data of the color image data at the coordinates (x, y), Ir(x, y) denotes the infrared-component data of the pixel data of the color image data at the coordinates (x, y), and r2, r3, r4, g2, g3, g4, b2, b3, b4, ir2, ir3 and ir4 denote coefficients. The coefficients r2, g2, b2, and ir2 are determined so that $r2 \times R(\lambda) + g2 \times G(\lambda) + b2 \times B(\lambda) + ir2 \times IR(\lambda)$ is as close as possible to $R_O(\lambda)$, where $R(\lambda)$ denotes a spectral sensitivity of a red-component photoelectric conversion element of the photoelectric conversion elements that outputs the image pickup signal of the red component, $G(\lambda)$ denotes a spectral sensitivity of a green-component photoelectric conversion element of the photoelectric conversion elements that outputs the image pickup signal of the green component, $B(\lambda)$ denotes a spectral sensitivity of a blue-component photoelectric conversion element of the photoelectric conversion elements that outputs the image pickup signal of the blue component, $IR(\lambda)$ denotes a spectral sensitivity of an infrared-component photoelectric conversion element of the photoelectric conversion elements that outputs the image pickup signal of the infrared component, and $R_O(\lambda)$ denotes an ideal spectral sensitivity of a photoelectric conversion element that outputs an image pickup signal of the red component. The coefficients r3, g3, b3, and ir3 are determined so that $r3 \times R(\lambda) + g3 \times G(\lambda) + b3 \times B(\lambda) + ir3 \times IR(\lambda)$ is as close as possible to $G_O(\lambda)$, where $G_O(\lambda)$ denotes an ideal spectral sensitivity of a photoelectric conversion element that outputs an image pickup signal of the green component, and the coefficients r4, g4, b4, and ir4 are determined so that $r4 \times R(\lambda) + g4 \times G(\lambda) + b4 \times B(\lambda) + ir4 \times IR(\lambda)$ is as close as possible to $B_O(\lambda)$, where $G_O(\lambda)$ denotes an ideal spectral sensitivity of a photoelectric conversion element that outputs an image pickup signal of the blue component.

(16) In the image processing apparatus of any one of (14) to (15), wherein the image pickup device may include a large number of first photoelectric conversion elements, second photoelectric conversion elements, a color filter layer and a signal reading portion. The first photoelectric conversion elements are arranged on a first plane in a semiconductor substrate. The second photoelectric conversion elements are formed on a second plane, which is located above the first photoelectric conversion elements. The second photoelectric conversion elements correspond to a part of the large number of first photoelectric conversion elements. The second photoelectric conversion elements include first electrodes formed above the first photoelectric conversion elements. The photoelectric conversion layer formed on the first electrodes, and a second electrode formed on the photoelectric conversion layer. The color filter layer is formed above the first photoelectric conversion elements. The color filter layer transmits light in a wavelength range different from a wavelength range of light that the photoelectric conversion layer absorbs. The signal reading portion reads (i) signals that correspond to charges generated in the second photoelectric conversion elements and (ii) signals that correspond to charges generated in the first photoelectric conversion elements. The color filter layer includes a large number of color filters that correspond to the large number of photoelectric conversion elements, respectively. The large number of color filters are classified into three types of color filters of those for transmitting light in a red wavelength range, those for transmitting light in a green wavelength range, and those for transmitting light in a blue wavelength range. Of the three types of color filters, at least the color filters for transmitting light in the red wavelength range also transmit infrared region light. The photoelectric conversion layer absorbs the infrared region light to generate charges in response thereto, and transmits any other light than the infrared region light. The part of the large number of first photoelectric conversion elements are the first photoelectric conversion elements corresponding to the color filters for transmitting light in the red wavelength range.

(17) In the image processing apparatus of (16), the color filter layer may be formed above the second photoelectric conversion elements.

(18) In the image processing apparatus of (17), the photoelectric conversion layer may contain an organic material. The image pickup device may further include a protective layer that protects the second photoelectric conversion elements. The protective layer is formed by an ALCVD method between the first photoelectric conversion elements and the color filter layer.

(19) In the image processing apparatus of (18), the protective layer may contain an inorganic material.

(20) In the image processing apparatus of (19), the protective layer may have a two-layer structure including an inorganic layer made of an inorganic material and an organic layer made of an organic polymer.

(21) In the image processing apparatus of any one of (16) to (20), the image pickup device may further include a microlens that collects light in each of the large number of first photoelectric conversion elements.

(22) According to another aspect of the invention, an endoscope includes an image processing apparatus; and the image processing apparatus of any one of (14) to (21).

(23) According to further another aspect of the invention, a computer readable medium stores a program for causing a computer to execute a process for image processing. The image processing includes: generating color image data from an image pickup signal of a red component, an image pickup signal of a green component, and an image pickup signal of a blue component which are output from an image pickup device; generating infrared image data from an image pickup signal of an infrared component output from the image pickup device; and generating high-color-reproduction color image data using the color image data and the infrared image data. The high-color-reproduction color image data has color reproducibility higher than the color image data.

According to any of the above configurations of (14) to (23), there can be provided an image processing apparatus capable of generating RGB color image data good in color reproducibility from the image pickup signal from the image pickup device without providing an IR cut filter in front of the image pickup device, an endoscope and a computer readable medium storing an image processing program.

BRIEF DESCRIPTION OF THE DRAWINGS

FIG. 13 is a drawing to show characteristic obtained by performing a process of bringing the characteristic of R second photoelectric conversion element of the image pickup device shown in FIG. 1 to be close to the characteristic shown in Real curve in FIG. 12;

FIG. 14 is a drawing to show the detection sensitivity characteristic of hemoglobin when an image is picked up with the image pickup device having the characteristic shown in FIG. 13;

FIG. 16 is a drawing to show the detection sensitivity characteristic of hemoglobin when an image is picked up with the image pickup device having the characteristic shown in FIG. 15;

DETAILED DESCRIPTION OF EMBODIMENTS OF THE INVENTION

Referring now to the accompanying drawings, embodiments of the invention will be described below.

First Embodiment

Figure 1:
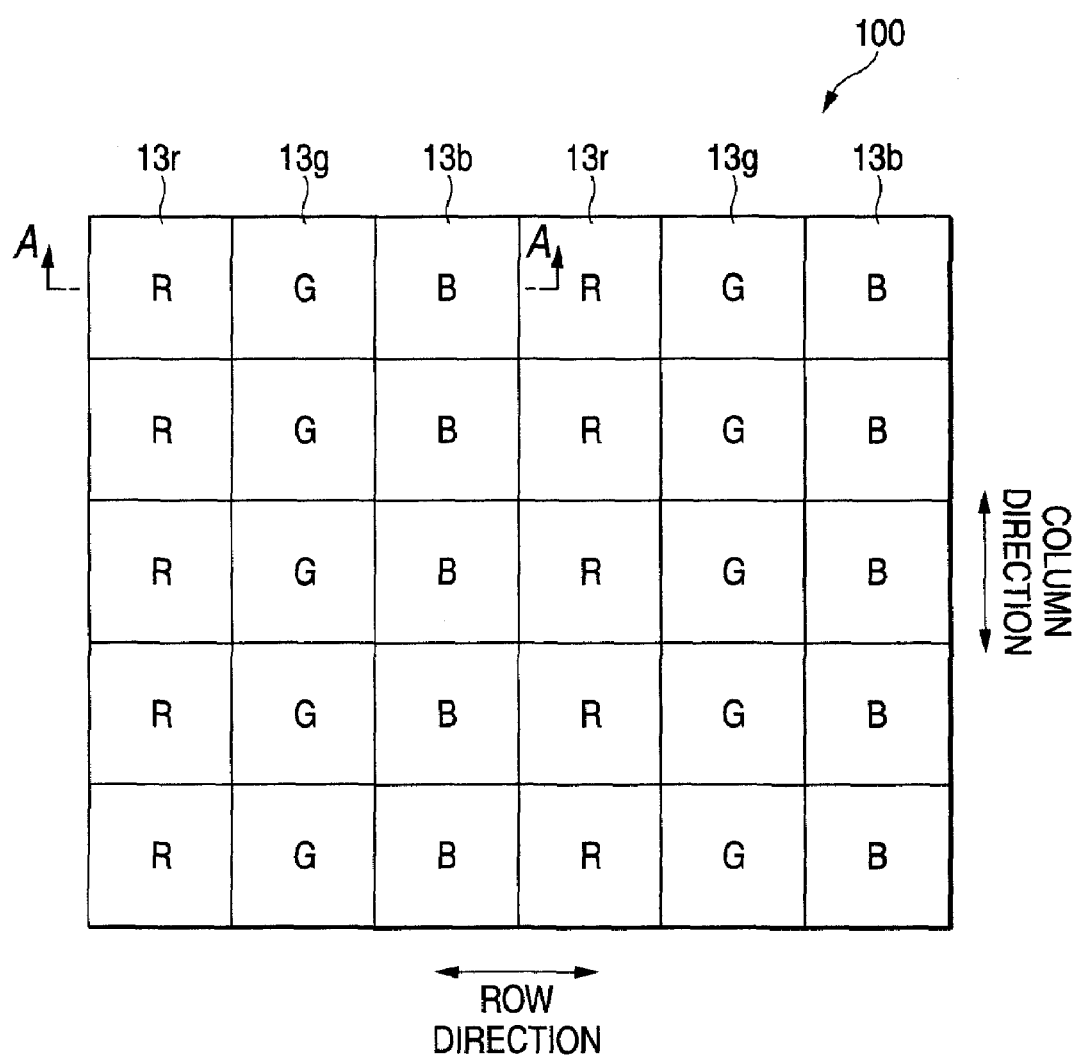
FIG. 1 is a partial schematic diagram of a surface of an image pickup device to describe an embodiment of the invention.
Figure 2:
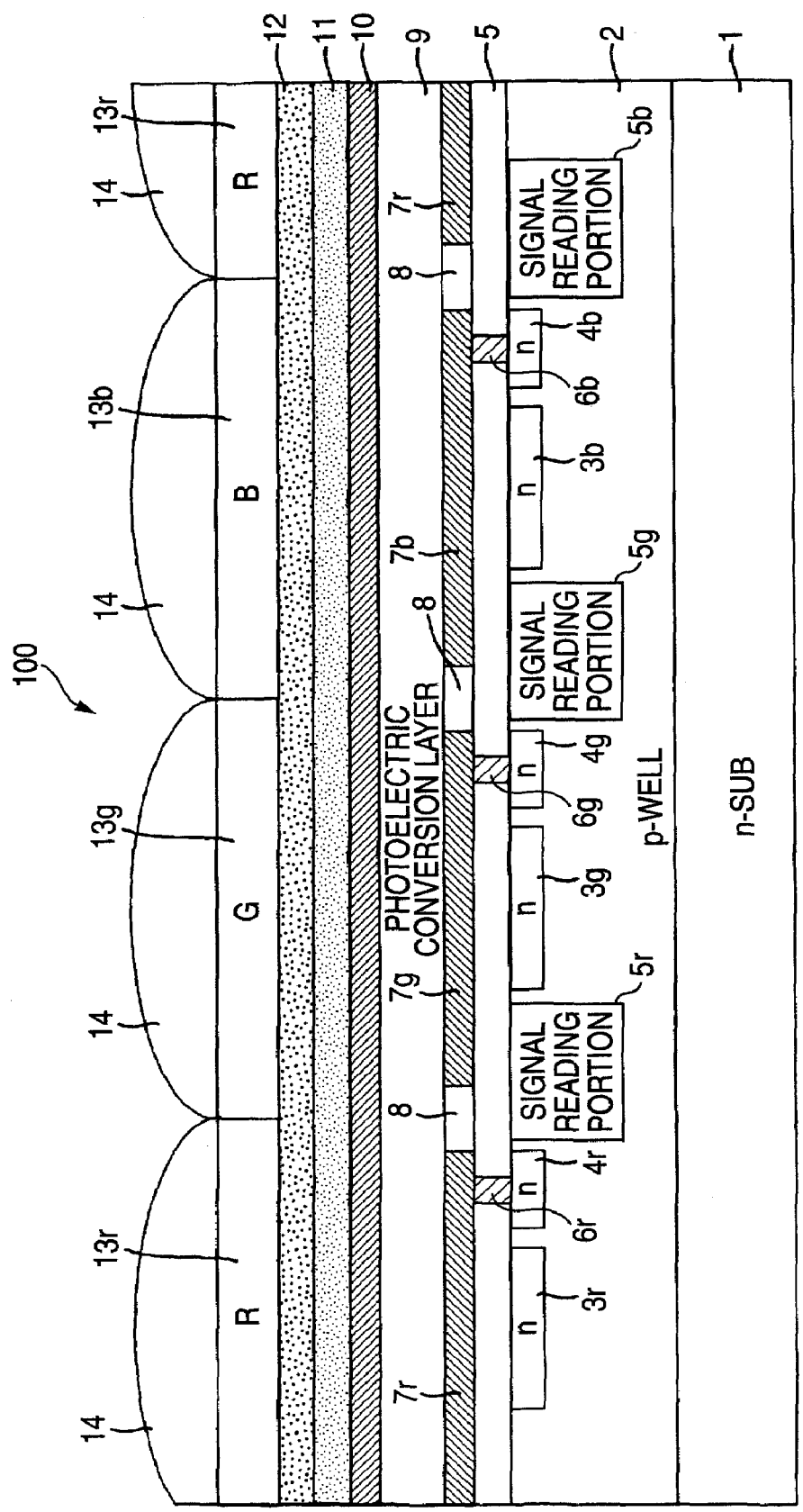
FIG. 2 is a sectional schematic diagram of the image pickup device taken along a line A-A in FIG. 1.

FIG. 1 is a partial schematic diagram of a surface of an image pickup device to describe an embodiment of the invention. FIG. 2 is a sectional schematic diagram of the image pickup device taken along a line A-A in FIG. 1. In FIG. 1, a microlens 14 is not shown.

A p-well layer 2 is formed on an n-type silicon substrate 1. In the following description, the n-type silicon substrate 1 and the p-well layer 2 are collectively called a semiconductor substrate. Three types of color filters, namely, a large number of color filters 13r for mainly transmitting light of R wavelength range, a large number of color filters 13g for mainly transmitting light of G wavelength range, and a large number of color filters 13b for mainly transmitting light of B wavelength range are arranged in a row direction and in a column direction perpendicular to the row direction on the same plane above the semiconductor substrate.

Although a known material may be used as the color filter 13r, such a material also transmits a part of light of infrared region as well as light of R wavelength range. Although a known material may be used as the color filter 13g, such a material also transmits a part of light of infrared region in addition to light of G wavelength range. Although a known material may be used as the color filter 13b, such a material also transmits a part of light of infrared region in addition to light of B wavelength range.

Color filter arrangement used in a known single plate CCD (Bayer arrangement, longitudinal stripe, lateral stripe, etc.,) may be adopted for the arrangement of the color filter 13r, 13g, 13b.

An n-type impurity region (n region) 3r is formed in the p-well layer 2 below the color filter 13r so as to correspond to the color filter 13r, and a pn junction between the n region 3r and the p-well layer 2 forms an R first photoelectric conversion element corresponding to the color filter 13r.

An n region 3g is formed in the p-well layer 2 below the color filter 13g so as to correspond to the color filter 13g, and a pn junction between the n region 3g and the p-well layer 2 forms a G first photoelectric conversion element corresponding to the color filter 13g.

An n region 3b is formed in the p-well layer below the color filter 13b so as to correspond to the color filter 13b, and a pn junction between the n region 3b and the p-well layer 2 forms a B first photoelectric conversion element corresponding to the color filter 13b.

A transparent electrode 7r is formed above the n region 3r, a transparent electrode 7g is formed above the n region 3g, and a transparent electrode 7b is formed above the n region 3b. The transparent electrodes 7r, 7g, and 7b are divided correspondingly to the color filters 13r, 13g, and 13b, respectively. Each of the transparent electrodes 7r, 7g, and 7b is formed of a material which is transparent for both of visible light and infrared light. For example, ITO, IZO, etc., may be used. Each of the transparent electrodes 7r, 7g, and 7b is buried in an insulating layer 8.

Formed on the transparent electrodes 7r, 7g, and 7b is a photoelectric conversion layer 9 of a one-sheet structure common to the color filters 13r, 13g, and 13b. The photoelectric conversion layer 9 mainly absorbs infrared-region light of wavelength 580 nm or more, generates charges in response thereto and transmits light of visible region other than the infrared region (wavelength in a range of about 380 nm to about 580 nm). For example, a phthalocyanine-based organic material or a naphthalocyanine-based organic material is used as a material forming the photoelectric conversion layer 9.

A transparent electrode 10 having a one-sheet structure common to the color filters 13r, 13g, and 13b is formed on the photoelectric conversion layer 9. The transparent electrode 10 is formed of a transparent material for both of visible light and infrared light. For example, ITO, IZO, etc., may be used.

The transparent electrode 7r, the transparent electrode 10 facing the transparent electrode 7r, and a part of the photoelectric conversion layer 9 sandwiched therebetween form a photoelectric conversion element corresponding to the color filter 13r. Hereinafter, this photoelectric conversion element will be referred to as an R second photoelectric conversion element.

The transparent electrode 7g, the transparent electrode 10 facing the transparent electrode 7g, and a part of the photoelectric conversion layer 9 sandwiched therebetween form a photoelectric conversion element corresponding to the color filter 13g. Hereinafter, this photoelectric conversion element may be called a G second photoelectric conversion element.

The transparent electrode 7b, the transparent electrode 10 facing the transparent electrode 7b, and a part of the photoelectric conversion layer 9 sandwiched therebetween form a photoelectric conversion element corresponding to the color filter 13b. Hereinafter, this photoelectric conversion element may be called a B second photoelectric conversion element.

A high-concentration n-type impurity region (which will be hereinafter referred to as n+ region) 4r is formed adjacent to the n region 3r in the p-well layer 2 to store charges generated in the photoelectric conversion layer 9 of the R second photoelectric conversion element. To prevent light from entering the n+ region 4r, preferably a shading film is provided on the n+ region 4r.

An n+ region 4g is formed adjacent to the n region 3g in the p-well layer 2 to store charges generated in the photoelectric conversion layer 9 of the G second photoelectric conversion element. To prevent light from entering the n+ region 4g, preferably a shading film is provided on the n+ region 4g.

An n+ region 4b is formed adjacent to the n region 3b in the p-well layer 2 to store charges generated in the photoelectric conversion layer 9 of the B second photoelectric conversion element. To prevent light from entering the n+ region 4b, preferably a shading film is provided on the n+ region 4b.

A contact portion 6r made of a metal such as aluminum is formed on the n+ region 4r, and the transparent electrode 7r is formed on the contact portion 6r. As a result, the n+ region 4r and the transparent electrode 7r are electrically connected by the contact portion 6r. The contact portion 6r is buried in the insulating layer 5 transparent for both of visible light and infrared light.

A contact portion 6g made of a metal such as aluminum is formed on the n+ region 4g, and the transparent electrode 7g is formed on the contact portion 6g. As a result, the n+ region 4g and the transparent electrode 7g are electrically connected by the contact portion 6g. The contact portion 6g is buried in the insulating layer 5.

A contact portion 6b made of a metal such as aluminum is formed on the n+ region 4b, and the transparent electrode 7b is formed on the contact portion 6b. As a result, the n+ region 4b and the transparent electrode 7b are electrically connected by the contact portion 6b. The contact portion 6b is buried in the insulating layer 5.

A signal reading portion 5r for reading signals corresponding to the charges which are generated in the R photoelectric conversion element and which are stored in the n region 3r and signals corresponding to the charges stored in the n+ region 4r, a signal reading portion 5g for reading signals corresponding to the charges which are generated in the G photoelectric conversion element and which are stored in the n region 3g and signals corresponding to the charges stored in the n+ region 4g, and a signal reading portion 5b for reading signals corresponding to the charges which are generated in the B photoelectric conversion element and which are stored in the n region 3b and signals corresponding to the charges stored in the n+ region 4b are formed in other regions than the n region 3r, 3g, 3b or the n+ region 4r, 4g, 4b in the p-well layer 2. A known configuration using a CCD or a MOS circuit may be adopted for each of the signal reading portions 5r, 5g, and 5b. To prevent light from entering the signal reading portion 5r, 5g, 5b, preferably a shading film is provided on the signal reading portion 5r, 5g, 5b.

Figure 3:
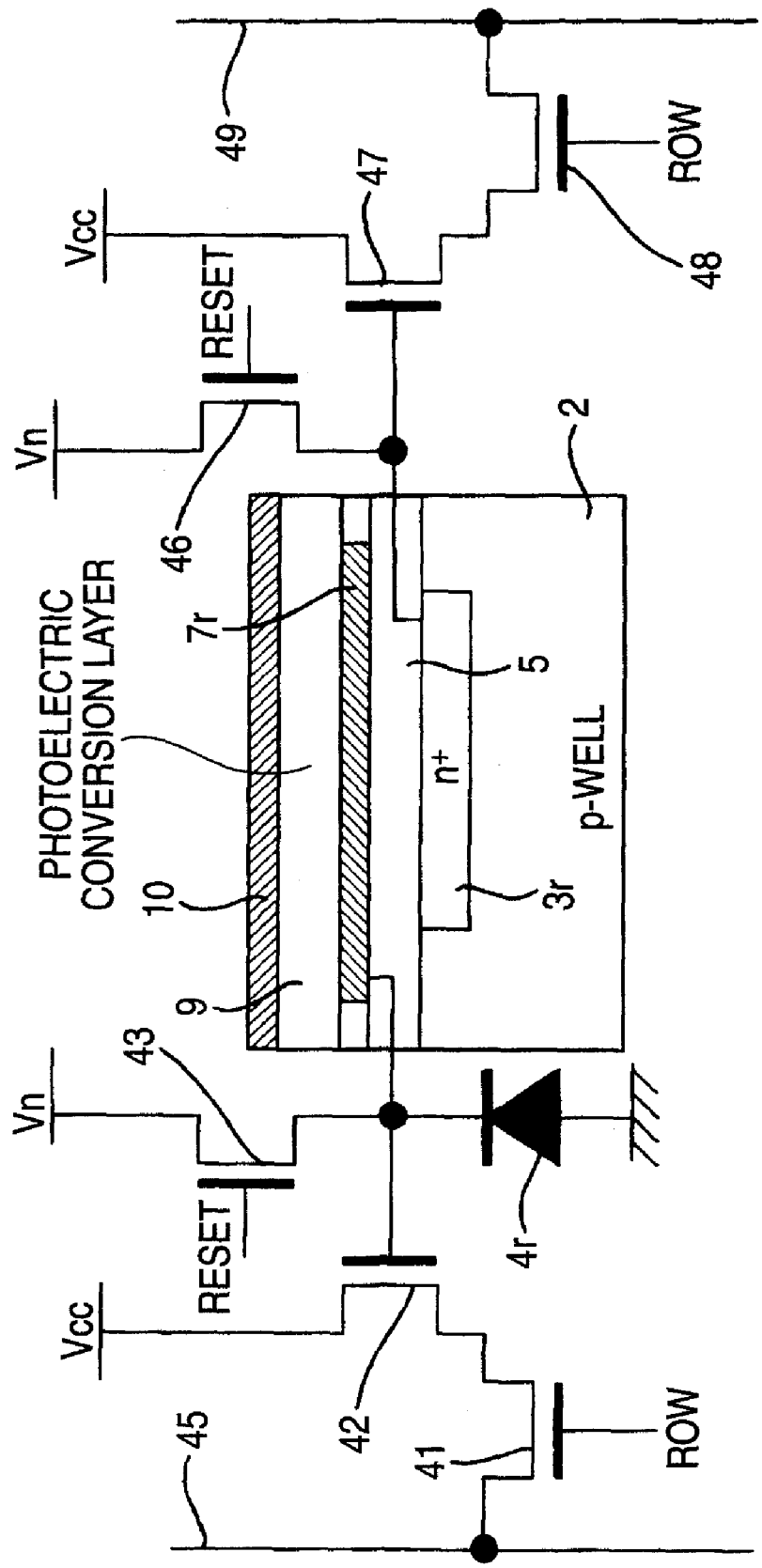
FIG. 3 is a drawing to show a specific configuration example of a signal reading portion 5r shown in FIG. 2.

FIG. 3 is a drawing to show a specific configuration example of the signal reading portion 5r shown in FIG. 2. Components similar to those in FIGS. 1 and 2 are denoted by the same reference numerals in FIG. 3. The configurations of the signal reading portions 5r, 5g, and 5b are identical, and therefore the signal reading portions 5g and 5b will not be described.

The signal reading portion 5r includes a rest transistor 43, an output transistor 42, a row selection transistor 41, a rest transistor 46, an output transistor 47 and a row selection transistor 48. The reset transistor 43 has a drain connected to the n+ region 4r and a source connected to power supply Vn. The output transistor 42 has a gate connected to the drain of the reset transistor 43 and a source connected to a power supply Vcc. The row selection transistor 41 has a source connected to the drain of the output transistor 42 and a drain connected to a signal output line 45. The reset transistor 46 has a drain connected to the n region 3r and a source connected to the power supply Vn. The output transistor 47 has a gate connected to the drain of the reset transistor 46 and a source connected to the power supply Vcc. The row selection transistor 48 has a source connected to the drain of the output transistor 47 and a drain connected to a signal output line 49.

When a bias voltage is applied between the transparent electrode 7r and the transparent electrode 10, charges are generated in response to the light incident on the photoelectric conversion layer 9 and move through the transparent electrode 7r to the n+ region 4r. The charges stored in the n+ region 4r are converted into signals corresponding to the charge amount by the output transistor 42. When the row selection transistor 41 is turned ON, the signals are output to the signal output line 45. After the signal is output, the charges in the n+ region 4r are reset by the reset transistor 43.

The charges generated in the R photoelectric conversion element and stored in the n region 3r are converted into signals corresponding to the charge amount, by the output transistor 47. When the row selection transistor 48 is turned ON, the signals are output to the signal output line 49. After the signals are output, the charges in the n region 3r are reset by the reset transistor 46.

Thus, the signal reading portion 5r can be configured using a known MOS circuit including three transistors.

Referring back to FIG. 2, protective layers 11 and 12 having a two-layer structure to protect the second photoelectric conversion elements are formed above the photoelectric conversion layer 9, the color filters 13r, 13g, and 13b are formed on the protective layer 12, and microlenses 14 for collecting light in the corresponding n regions 3r, 3g, and 3b are formed on the color filters 13r, 13g, and 13b.

To manufacture the image pickup device 100, the photoelectric conversion layer 9 is formed and then the color filters 13r, 13g, and 13b, the microlenses 14, etc., are formed. Since the color filters 13r, 13g, and 13b and the microlenses 14 involve a photolithography step and a baking step, if an organic material is used as the photoelectric conversion layer 9, and the photolithography step and the baking step are executed with the photoelectric conversion layer 9 exposed, the characteristic of the photoelectric conversion layer 9 would be deteriorated. The image pickup device 100 is provided with the protective layers 11 and 12 to prevent characteristic deterioration of the photoelectric conversion layer 9 during the manufacturing steps.

Preferably, the protective layer 11 is an inorganic layer made of an inorganic material formed by an ALCVD method. The ALCVD method is an atomic layer CVD method and can form a tight inorganic layer; an effective protective layer for the photoelectric conversion layer 9 can be provided. The ALCVD method is also known as ALE method or ALD method. Preferably, the inorganic layer formed by the ALCVD method is made of $Al_2O_3$, $SiO_2$, $TiO_2$, $ZrO_2$, MgO, $HfO_2$, $Ta_2O_5$; more preferably, $Al_2O_3$, $SiO_2$; most preferably, $Al_2O_3$.

The protective layer 12 is formed on the protective layer 11 for the purpose of further improving the protective performance of the photoelectric conversion layer 9. Preferably, the protective layer 12 is an organic layer made of an organic polymer. Preferably, the organic polymer is perylene; more preferably, perylene C. The protective layer 12 may be omitted. The protective layers 11 and 12 may be placed in an opposite manner. The configuration shown in FIG. 2 provides a particularly high protection effect of the photoelectric conversion layer 9.

In the image pickup device 100 described above, infrared-region light of light passing through the color filter 13r, of incident light is absorbed by the photoelectric conversion layer 9 where charges responsive to the infrared-region light are generated. Likewise, infrared-region light of light passing through the color filter 13g, of the incident light is absorbed by the photoelectric conversion layer 9 where charges responsive to the infrared-region light are generated. Likewise, infrared-region light of light passing through the color filter 13b, of the incident light is absorbed by the photoelectric conversion layer 9 where charges responsive to the infrared region light are generated.

When a predetermined bias voltage is applied to the transparent electrode 7r and the transparent electrode 10, the charges generated in the photoelectric conversion layer 9 that forms the R second photoelectric conversion element move through the transparent electrode 7r and the contact portion 6r to the n+ region 4r where the charges are stored. The signals corresponding to the charges stored in the n+ region 4r are read by the signal reading portion 5r and are output to the outside of the image pickup device 100.

Likewise, when a predetermined bias voltage is applied to the transparent electrode 7g and the transparent electrode 10, charges generated in the photoelectric conversion layer 9 that forms the G second photoelectric conversion element move through the transparent electrode 7g and the contact portion 6g to the n+ region 4g where the charges are stored. The signals corresponding to the charges stored in the n+ region 4g are read by the signal reading portion 5r and are output to the outside of the image pickup device 100.

Likewise, when a predetermined bias voltage is applied to the transparent electrode 7b and the transparent electrode 10, charges generated in the photoelectric conversion layer 9 that forms the B second photoelectric conversion element move through the transparent electrode 7b and the contact portion 6b to the n+ region 4b where the charges are stored. The signals corresponding to the charges stored in the n+ region 4b are read by the signal reading portion 5b and are output to the outside of the image pickup device 100.

R wavelength range light passing through the color filter 13r and passing through the photoelectric conversion layer 9 is incident on the R first photoelectric conversion element and charges responsive to the incident light amount are stored in the n region 3r. Likewise, G wavelength range light passing through the color filter 13g and passing through the photoelectric conversion layer 9 is incident on the G first photoelectric conversion element and charges responsive to the incident light amount are stored in the n region 3g. Likewise, B wavelength range light passing through the color filter 13b and passing through the photoelectric conversion layer 9 is incident on the B first photoelectric conversion element and charges responsive to the incident light amount are stored in the n region 3b. The charges stored in the n regions 3r, 3g, and 3b are read by the signal reading portions 5r, 5g, and 5b and are output to the outside of the image pickup device 100.

The arrangement of the signals read and output from the n regions 3r, 3g, and 3b becomes similar to the arrangement of the signals output from a single plate color CCD having a color filter arrangement as shown in FIG. 1. Thus, when signal processing used in the single plate color CCD is performed, color image data in which each pixel data has three-color-component (R, G, and B) data can be generated. Also, infrared image data in which each pixel data has an infrared color component data can be generated from the signals read and output from the n+ regions 4r, 4g, and 4b.

In this manner, the image pickup device 100 can output the R component signal corresponding to the charges generated in the R first photoelectric conversion element, the G component signal corresponding to the charges generated in the G first photoelectric conversion element, the B component signal corresponding to the charges generated in the B first photoelectric conversion element, the IR component signal corresponding to the charges generated in the R second photoelectric conversion element, the IR component signal corresponding to the charges generated in the G second photoelectric conversion element, and the IR component signal corresponding to the charges generated in the B second photoelectric conversion element to the outside. Thus, the image pickup device 100 can provide two types of image data, that is, color image data and infrared image data by one image picking up process. Therefore, for example, the image pickup device 100 can be used as an image pickup device of an endoscope which is required to capture an appearance image of a part of a human being to be tested and an internal image of the part.

Next, the spectral sensitivity characteristic of the image pickup device 100 will be described.

Figure 4:
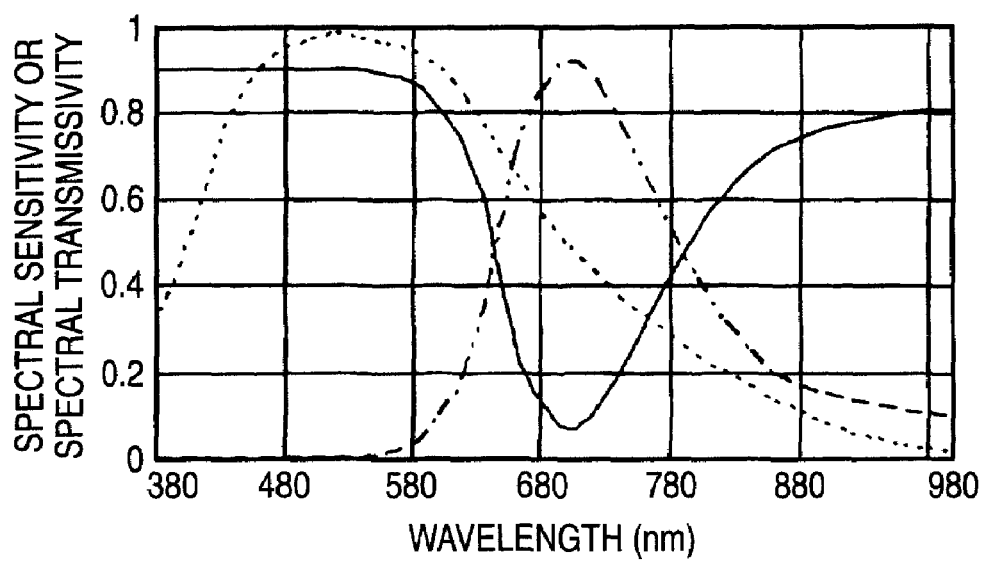
FIG. 4 is a drawing to show the characteristics of first photoelectric conversion elements and second photoelectric conversion elements of the image pickup device shown in FIG. 1.
Figure 5:
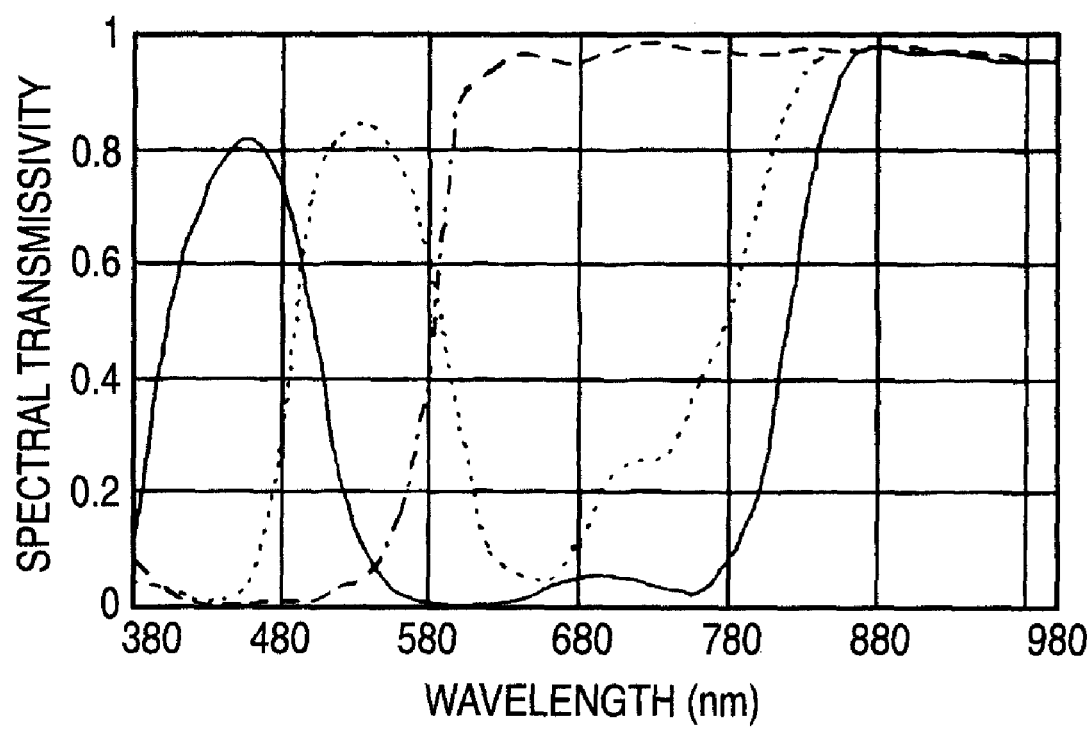
FIG. 5 is a drawing to show the characteristics of color filters of the image pickup device shown in FIG. 1.

First, it is assumed that the spectral sensitivity characteristic of each first photoelectric conversion element (PD) formed in the semiconductor substrate is as shown in FIG. 4, that the spectral sensitivity characteristic of the photoelectric conversion layer 9 is as shown in FIG. 4, that the spectral transmissivity of the photoelectric conversion layer 9 is as shown in FIG. 4, and that the spectral transmissivitys of the color filters 13r, 13g, and 13b are as shown in FIG. 5. In FIG. 4, the vertical axis indicates the spectral sensitivity or the spectral transmissivity where 1 is used as a reference, and the horizontal axis indicates the wavelength of light. In FIG. 5, the vertical axis indicates the spectral transmissivity where 1 is used as a reference, and the horizontal axis indicates the wavelength of light.

Figure 6:
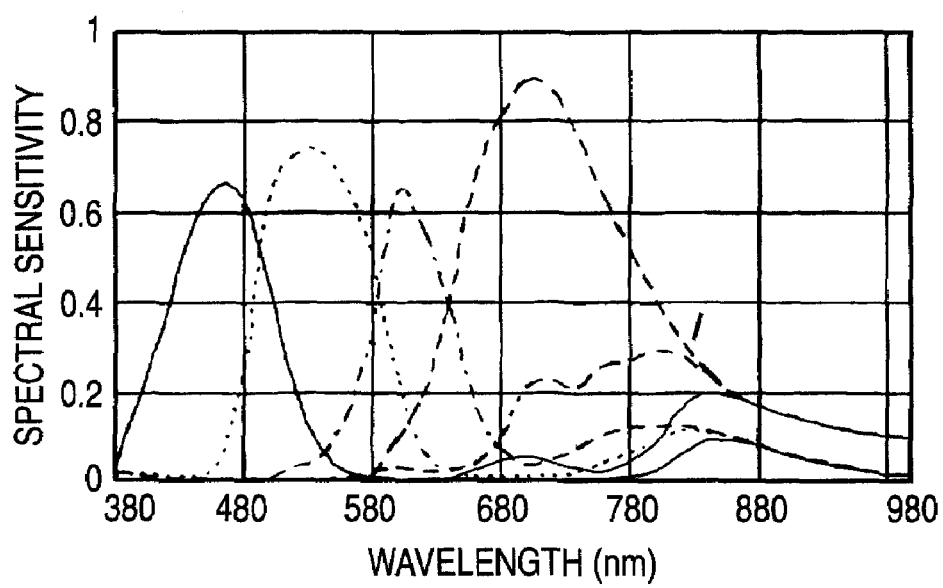
FIG. 6 is a drawing to show the characteristics of the image pickup device shown in FIG. 1 with no correction filter.

When the characteristic is thus determined, the spectral sensitivity characteristic of the R first photoelectric conversion element becomes a product of the spectral sensitivity of the first photoelectric conversion element (PD), the spectral transmissivity of the photoelectric conversion layer 9 and the spectral transmissivity of the color filter 13r; the spectral sensitivity characteristic of the G photoelectric conversion element becomes the product of the spectral sensitivity of the first photoelectric conversion element (PD), the spectral transmissivity of the photoelectric conversion layer 9 and the spectral transmissivity of the color filter 13g, and the spectral sensitivity characteristic of the B photoelectric conversion element becomes the product of the spectral sensitivity of the first photoelectric conversion element (PD), the spectral transmissivity of the photoelectric conversion layer 9 and the spectral transmissivity of the color filter 13b, as shown in FIG. 6. In FIG. 6, the vertical axis indicates the spectral sensitivity when 1 is the reference, and the horizontal axis indicates the wavelength of light.

The spectral sensitivity characteristic of the R second photoelectric conversion element becomes the product of the spectral sensitivity of the photoelectric conversion layer 9 and the spectral transmissivity of the color filter 13r, the spectral sensitivity characteristic of the G second photoelectric conversion element becomes the product of the spectral sensitivity of the photoelectric conversion layer 9 and the spectral transmissivity of the color filter 13g, and the spectral sensitivity characteristic of the B second photoelectric conversion element becomes the product of the spectral sensitivity of the photoelectric conversion layer 9 and the spectral transmissivity of the color filter 13b, as shown in FIG. 6.

Figure 7:
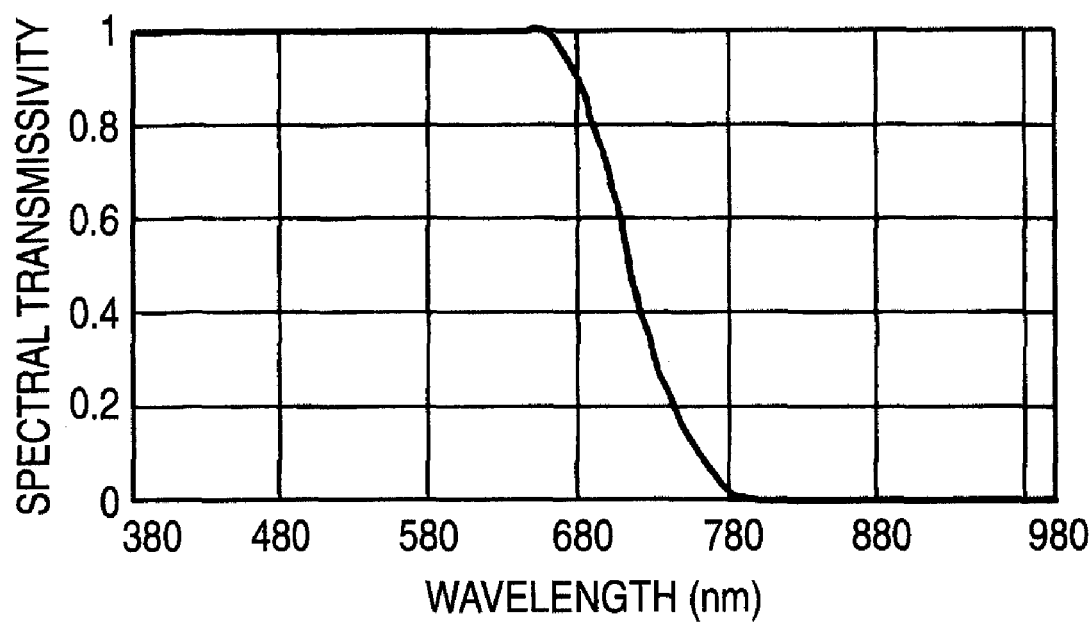
FIG. 7 is a drawing to show the characteristics of a correction filter.
Figure 8:
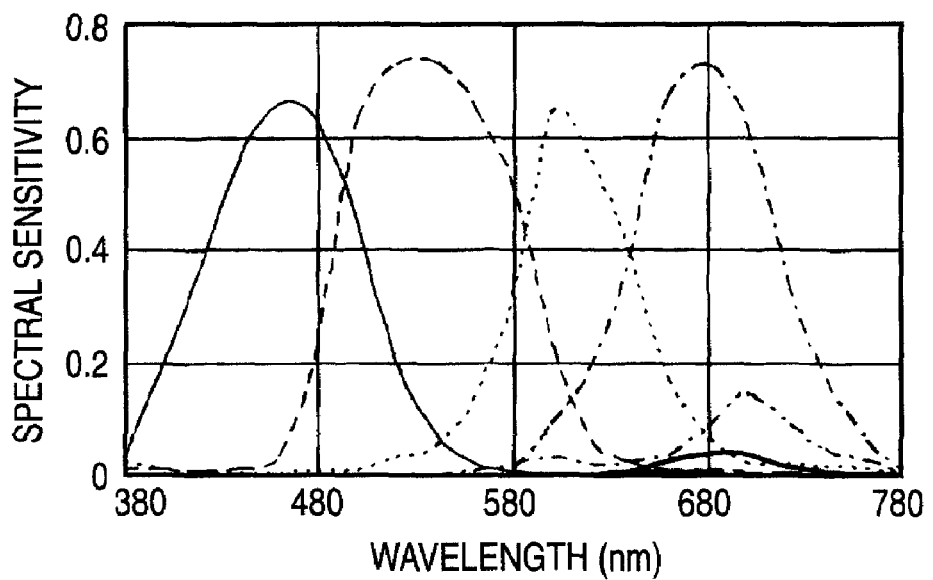
FIG. 8 is a drawing to show the characteristics of the image pickup device shown in FIG. 1 with the correction filter.

Here, to adjust the spectral sensitivity characteristic of each second photoelectric conversion element, if a correction filter having a spectral transmissivity as shown in FIG. 7 is placed on the light incident face side of the image pickup device 100, the spectral sensitivity characteristic of the image pickup device 100 becomes as shown in FIG. 8. In FIG. 7, the vertical axis indicates the spectral transmissivity where 1 is used as a reference, and the horizontal axis indicates the wavelength of light. In FIG. 8, the vertical axis indicates the spectral sensitivity where 1 is used as a reference, and the horizontal axis indicates the wavelength of light.

Figure 9:
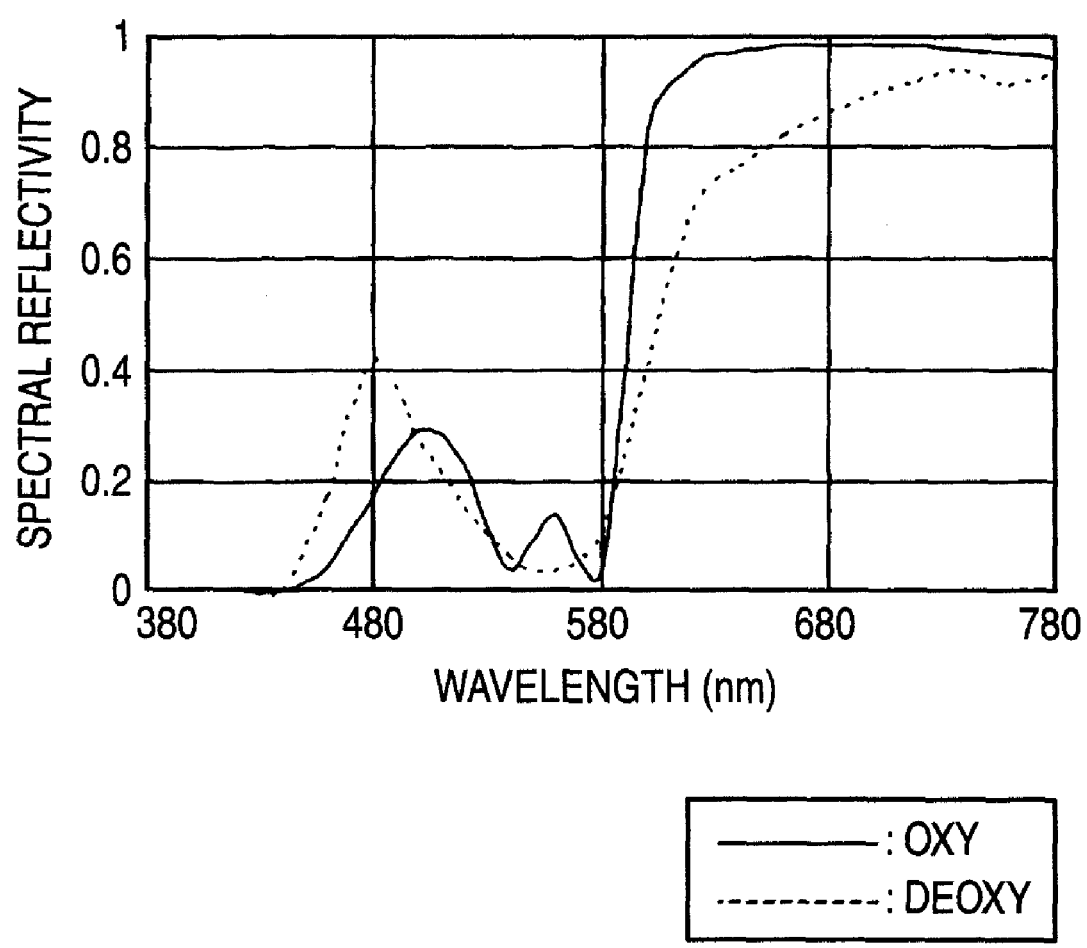
FIG. 9 is a drawing to show the spectral reflectivity of hemoglobin.

FIG. 9 is a drawing to show the spectral reflectivity of oxygenated hemoglobin (oxy) and reduced hemoglobin (deoxy). In FIG. 9, the vertical axis indicates the spectral reflection factor where 1 is used as a reference, and the horizontal axis indicates the wavelength of light.

As can be seen in FIG. 9, the reflectivity difference between oxygenated hemoglobin and reduced hemoglobin becomes large in the wavelength range of wavelengths 580 nm to 780 nm. Thus, if a photoelectric conversion element having sensitivity in this wavelength range is used, state change of hemoglobin can be put into an image with high contrast. The image pickup device 100 has the R second photoelectric conversion element having strong sensitivity in the wavelength range of wavelengths 580 nm to 780 nm as shown in FIG. 8. Therefore, when infrared image data is generated using the signals obtained from the R second photoelectric conversion element, it is made possible to provide an RGB color appearance image of the part to be tested and state change of hemoglobin of the part by a single image picking up process.

In the case where infrared image data is generated using the signals obtained only from the R second photoelectric conversion element, a signal may be interpolated, at positions of the signals obtained from the G second photoelectric conversion element and the B second photoelectric conversion element, using the signals obtained from the R second photoelectric conversion element on the periphery of the positions to generate infrared image data having the same resolution as color image data. Alternatively, only the signals obtained from the R second photoelectric conversion element may be used to generate infrared image data having one-third resolution of color image data. Further alternatively, the signals obtained from the three photoelectric conversion elements of the R second photoelectric conversion element, the G second photoelectric conversion element, and the B second photoelectric conversion element aligning in the row direction may be added to form one signal and infrared image data having one-third resolution of color image data may be generated based on this signal.

When this image pickup device 100 is used, the two types of image data, that is, color image data and infrared image data can be obtained. Such an effect can also be achieved if a complementary color system other than the primary color system is used as the color filters used with the image pickup device 100. Although the two types of image data cannot be obtained, if the color arrangement of the color filters of the image pickup device 100 and the wavelength range of light to be absorbed in the photoelectric conversion layer are adjusted, it is also made possible to provide RGB image data having higher resolution than a single plate image pickup device. FIG. 10 shows configuration examples of the image pickup device 100 to produce the effects. In FIG. 10, first photoelectric conversion elements (PD) formed in semiconductor substrate, second photoelectric conversion layer formed above the PD, and color filters formed above the photoelectric conversion layer are only shown as the components of the image pickup device 100.

An image pickup device shown in FIG. 10(*a*) is provided by changing the color filter 13*r* to a Cy filter for transmitting light in the wavelength range of Cy (cyan) and a part of infrared region light, changing the color filter 13*g* to an Mg filter for transmitting light in the wavelength range of Mg (magenta) and a part of infrared region light, and changing the color filter 13*b* to a Ye filter for transmitting light in the wavelength range of Ye (yellow) and a part of infrared region light in the image pickup device 100 shown in FIGS. 1 and 2. The Cy filter, the Mg filter, and the Ye filter may be made of known materials.

With this configuration, color image data can be generated from the Cy, Mg, and Ye signals obtained from the photoelectric conversion elements in the semiconductor substrate and infrared image data can be generated from the signals obtained from the photoelectric conversion layer. The arrangement of the Cy filter, the Mg filter, and the Ye filter may be any so long as a color image can be reproduced.

An image pickup device shown in FIG. 10(*b*) is provided by changing the color filter 13*r* to a Cy filter and changing the color filter 13*b* to a Ye filter in the image pickup device 100 shown in FIGS. 1 and 2.

With this configuration, color image data can be generated from the Cy, G, and Ye signals obtained from the photoelectric conversion elements in the semiconductor substrate and infrared image data can be generated from the signals obtained from the photoelectric conversion layer. The arrangement of the Cy filter, the G filter, and the Ye filter may be any so long as a color image can be reproduced.

An image pickup device shown in FIG. 10(*c*) is provided by changing the color filter 13*r* to a Cy filter, changing the color filter 13*g* to an IR filter for transmitting infrared region light, changing the photoelectric conversion layer 9 to a G photoelectric conversion layer for absorbing light in the wavelength range of G, generating signal charges responsive thereto, and transmitting light other than light in the wavelength range of G, and changing the color filter 13*b* to a Ye filter in the image pickup device 100 shown in FIGS. 1 and 2. As a material forming the G photoelectric conversion layer, InGaAlP or GaPAs may be used, for example, as an inorganic material; R6G/PMPS (rhodamine 6G (R6G)-doped polymethylphenylsilane) may be used, for example, as an organic material.

With this configuration, color image data can be generated from the B and R signals obtained from the photoelectric conversion elements in the semiconductor substrate and the G signal obtained from the photoelectric conversion layer, and infrared image data can be generated from the IR signal obtained from the photoelectric conversion layer below the IR filter. The arrangement of the Cy filter and the Ye filter may be any so long as a color image can be reproduced, and the arrangement of the Ir filter may be any so long as an infrared image can be reproduced.

An image pickup device shown in FIG. 10(*d*) is provided by changing the color filters 13*r* and 13*b* to Cy filters, changing the color filter 13*g* to a Ye filter, and changing the photoelectric conversion layer 9 to a G photoelectric conversion layer in the image pickup device 100 shown in FIGS. 1 and 2.

With this configuration, color image data can be generated from the B and R signals obtained from the photoelectric conversion elements in the semiconductor substrate and the G signal obtained from the photoelectric conversion layer. In this configuration, primary color system signals of two colors can be obtained per image pickup point, so that the resolution can be improved as compared with a single plate image pickup device.

The case where the number of types of color filters used in the image pickup device 100 is two or three has been described. However, similar advantages can be achieved even if the number of types of color filters is four or more. The number of types of color filters may be one. In this case, a G color filter of a one-sheet configuration for transmitting light in the wavelength range of G may be provided in place of the color filters 13*r*, 13*g*, and 13*b*, for example, in the configuration shown in FIG. 2.

With this configuration, monochrome image data can be generated from the signals obtained from the photoelectric conversion elements in the semiconductor substrate, and infrared image data can be generated from the signals obtained from the photoelectric conversion layer 9. When this configuration is adopted, there is also the advantage that the spectral sensitivity characteristic of the photoelectric conversion layer can be adjusted according to the spectral transmissivity of the filter provided above the photoelectric conversion layer.

In the description given above, the photoelectric conversion layer is provided above the semiconductor substrate and the color filters are provided above the photoelectric conversion layer. However, similar advantages can be achieved even if the photoelectric conversion layer and the color filters are placed in an opposite manner.

In the description given above, the color filters 13*r*, 13*g*, and 13*b* transmit infrared region light. However, a filter having a spectral transmissivity not allowing infrared region light to pass through may also be used. However, if all color filters are those for not allowing infrared region light to pass through, it becomes impossible to generate infrared image data. Therefore, at least one of color filters of one type or more needs to be provided with a function of allowing infrared region light to pass through.

In the description given above, the three types of second photoelectric conversion elements, that is, R, G, and B second photoelectric conversion elements are provided. However, if at least one of them exists, it is sufficient to obtain infrared image data. As shown in FIGS. 6 and 8, the R second photoelectric conversion element has the most sensitivity in the infrared region and therefore most preferably, infrared image data is generated using the signal output from the R second photoelectric conversion element. In the case where the G second photoelectric conversion element is omitted, the transparent electrode 7*g*, the contact portion 6*g*, and the n+ region 4*g* may be omitted in the configuration shown in FIG. 2. In the case where the B second photoelectric conversion element is omitted, the transparent electrode 7*b*, the contact portion 6*b*, and the n+ region 4*b* may be omitted in the configuration shown in FIG. 2.

In the configuration shown in FIG. 10(*c*), if the second photoelectric conversion elements provided in the image pickup device are only the second photoelectric conversion elements corresponding to the IR filters, it is hard to obtain G component signals from the second photoelectric conversion elements and generation of color image data is hindered. Thus, in the configuration shown in FIG. 10(c), it is necessary to provide at least the second photoelectric conversion element corresponding to the Cy filter or the second photoelectric conversion element corresponding to the Ye filter.

Next, a method for manufacturing the image pickup device 100 will be described. The image pickup device 100 can be manufactured in the following processes (A) to (C):

(A) Formation of CMOS Substrate→Formation of Transparent Electrode

As with a conventional CMOS sensor, n regions 3r, 3g, and 3b and signal reading portions are formed on a silicon substrate.

Further, n+ regions 4r, 4g, and 4b and signal reading portions are formed.

Insulating layer 5 is formed on the silicon substrate, transparent electrodes 7r, 7g, and 7b are formed thereon, and the transparent electrodes 7r, 7g, and 7b and the n+ regions 4r, 4g, and 4b are brought into contact with each other using a via plug.

Insulating material is filled into gaps among the transparent electrodes 7r, 7g, and 7b and the surfaces of the transparent electrodes 7r, 7g, and 7b are made flat containing the insulating material portion using CMP.

This process is executed as a semiconductor process.

(B) Formation of Photoelectric Conversion Layer

Photoelectric conversion layer 9 is formed on the transparent electrodes 7r, 7g, and 7b.

Further, transparent electrode 10 is formed. The transparent electrode 10 is brought into contact with a pad (not shown), and a bias voltage is applied to the transparent electrode 10 from an external power supply.

This process is executed as a vacuum evaporation process.

(C) Formation of Microlenses and Color Filters

An alumina protective layer is formed on the photoelectric conversion layer 9 by the ALCVD method, for example, and further a perylene C protective layer is formed.

Next, a mosaic color filter is formed. The mosaic color filter is formed in order of G resist application→pattern exposure→developing→post bake, B resist application→pattern exposure→developing→post bake, →R resist application→pattern exposure→developing→post bake.

Last, microlenses are formed. The microlenses are formed in order of resist application→post bake→resist application→pattern exposure→developing, melt.

Second Embodiment

In a second embodiment of the invention, an image pickup device 100 capable of providing color image data and infrared image data as described in the first embodiment is applied to an endoscope.

Figure 11:
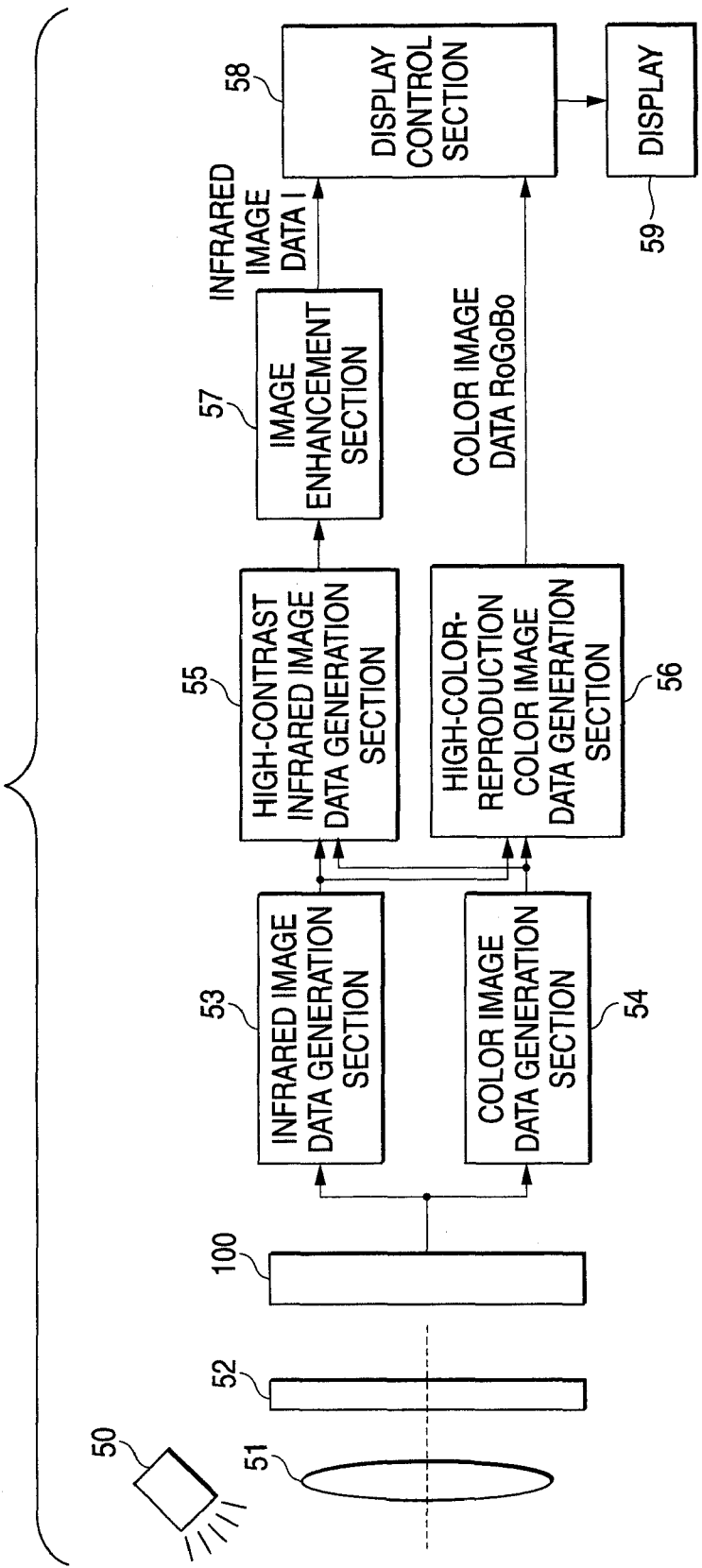
FIG. 11 is a drawing to show the schematic configuration of an endoscope to describe a second embodiment of the invention.

FIG. 11 is a drawing to show the schematic configuration of an endoscope to describe the second embodiment.

The endoscope shown in FIG. 11 includes a white light source 50, an optical system 51, the image pickup device 100, a correction filter 52, an infrared image data generation section 53, a color image data generation section 54, a high-contrast infrared image data generation section 55, a high-color-reproduction color image data generation section 56, an image enhancement section 57 and a display control section 58. The white light source 50 illuminates a part to be tested. The optical system 51 includes an imaging lens, an aperture diaphragm and the like. The image pickup device 100 has the configuration shown in FIGS. 1 and 2 and receives light passing through the optical system 51. The correction filter 52 is disposed between the image pickup device 100 and the optical system 51 and corrects the spectral sensitivity characteristic of the photoelectric conversion layer 9 of the image pickup device 100. The infrared image data generation section 53 generates infrared image data based on signals corresponding to charges generated in the photoelectric conversion layer 9 of the image pickup device 100. The color image data generation section 54 generates color image data based on signals corresponding to charges generated in the R, G, and B first photoelectric conversion elements of the image pickup device 100. The high-contrast infrared image data generation section 55 performs a computation process using the infrared image data generated by the infrared image data generation section 53 and the color image data generated by the color image data generation section 54 to generate high-contrast infrared image data that is more enhanced in contrast than the infrared image data generated by the infrared image data generation section 53. The image enhancement section 57 performs an enhancement process for the high-contrast infrared image data generated by the high-contrast infrared image data generation section 55. The high-color-reproduction color image data generation section 56 performs a computation process using the infrared image data generated by the infrared image data generation section 53 and the color image data generated by the color image data generation section 54 to generate high-color-reproduction color image data which has higher color reproducibility than the color image data generated by the color image data generation section 54. The display control section 58 controls a display 59 to display an image based on the high-contrast infrared image data for which the enhancement process is performed and to display an image based on the high-color-reproduction color image data.

Figure 10A:
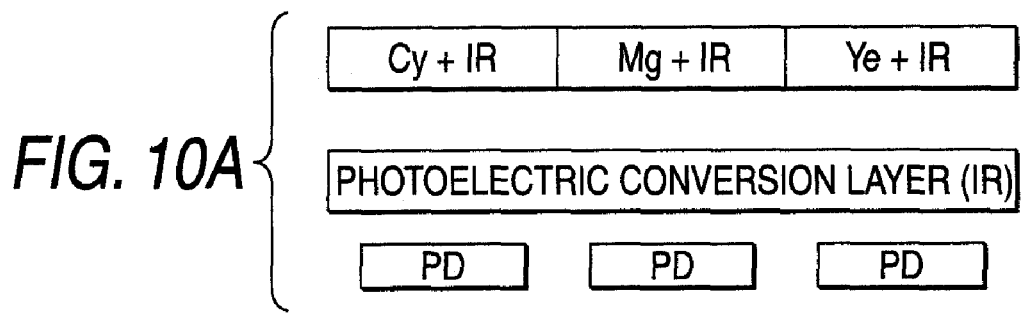
FIG. 10 is a drawing to show modified examples of the configuration of the image pickup device shown in FIG. 1.
Figure 10B:
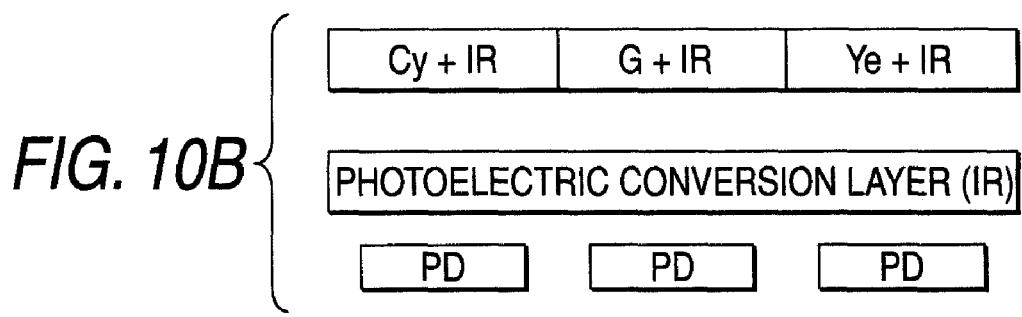
Figure 10C:
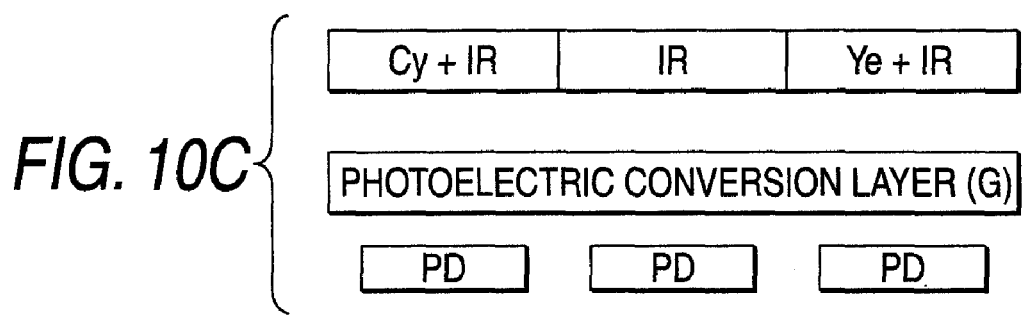
Figure 10D:
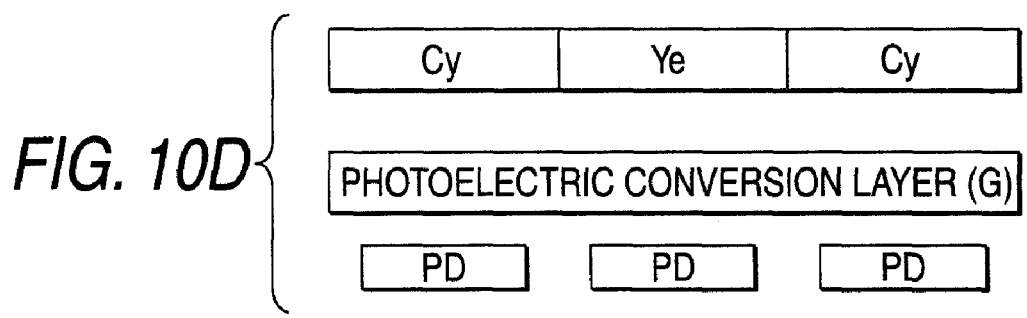

The image pickup device 100 for use in the endoscope shown in FIG. 11 may not limited to the configuration shown in FIGS. 1 and 2, but may be any so long as it can output the four types of signals of an R component signal corresponding to light in the wavelength range of R, a G component signal corresponding to light in the wavelength range of G, a B component signal corresponding to light in the wavelength range of B, and an IR component signal corresponding to infrared region light. For example, the image pickup device 100 may be an image pickup device having the configuration as shown in FIG. 10(c) or may be a single plate image pickup device in which a color filter for transmitting light in the wavelength range of R or Cy, a color filter for transmitting light in the wavelength range of G or Mg, a color filter for transmitting light in the wavelength range of B or Ye, and a color filter for transmitting infrared region light are arranged like a mosaic on the same plane above the semiconductor substrate. The spectral sensitivity characteristic of the image pickup device 100 may be one shown in FIG. 8, for example.

The color image data generation section 54 acquires, from the image pickup device 100, signals corresponding to charges generated in the R first photoelectric conversion element of the image pickup device 100 (which will be hereinafter referred to as an R signal), signals corresponding to charges generated in the G first photoelectric conversion element of the image pickup device 100 (which will be hereinafter referred to as a G signal), and signals corresponding to charges generated in the B first photoelectric conversion element of the image pickup device 100 (which will be hereinafter referred to as a B signal). The color image data generation section 54 uses these signals to generate color image data according to a known technique.

The infrared image data generation section 53 generates infrared image data having the same resolution as the color image data by performing signal interpolation, etc., from signals corresponding to charges generated in the R second photoelectric conversion element of the image pickup device 100 (which will be hereinafter referred to as an IRr signal).

Figure 12:
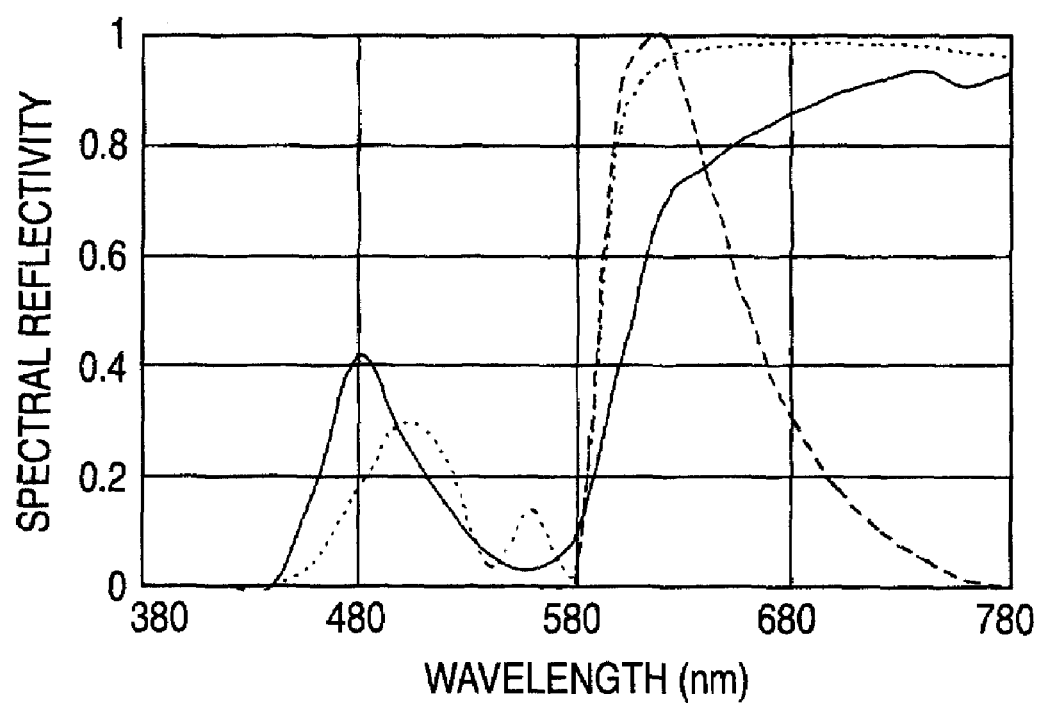
FIG. 12 is a drawing to show spectral reflectivity of hemoglobin and spectral sensitivity characteristic which makes it possible to detect a state change of hemoglobin with the highest contrast.

FIG. 12 is a drawing to show spectral reflectivities of oxygenated hemoglobin and reduced hemoglobin. In FIG. 12, the vertical axis indicates the spectral transmissivity where 1 is used as a reference, and the horizontal axis indicates the wavelength of light. In FIG. 12, the vertical axis also indicates the spectral sensitivity of a photoelectric conversion element where 1 is used as a reference. If an image of hemoglobin is picked up with the photoelectric conversion element having spectral sensitivity represented by a Real curve shown in FIG. 12, state change of hemoglobin can be detected with the highest contrast.

Then, the high-contrast infrared image data generation section 55 performs the computation process of bringing the IRr signal obtained from the R second photoelectric conversion element to be close to the signal obtained from the photoelectric conversion element having the spectral sensitivity characteristic represented by the Real curve shown in FIG. 12, to thereby improve the contrast of the infrared image data.

Specifically, the high-contrast infrared image data generation section 55 performs computation represented by the following expression (1) to generate high-contrast infrared image data:

$$I(x,y)=r1\times R(x,y)+g1\times G(x,y)+b1\times B(x,y)+ir1\times IR(x,y) \quad (1)$$

where I(x, y) denotes pixel data of high-contrast infrared image data at coordinates (x, y), R(x, y) denotes R component pixel data of the color image data at the coordinates (x, y), G(x, y) denotes G component pixel data of the color image data at the coordinates (x, y), B(x, y) denotes B component pixel data of the color image data at the coordinates (x, y), IR(x, y) denotes IR component pixel data of the infrared image data at the coordinates (x, y), and r1, g1, b1, and ir1 denote coefficients which are determined based on the spectral sensitivity characteristic of the R first photoelectric conversion element, the spectral sensitivity characteristic of the G first photoelectric conversion element, the spectral sensitivity characteristic of the B first photoelectric conversion element, the spectral sensitivity characteristic of the R second photoelectric conversion element, and the spectral sensitivity characteristic represented by the Real curve shown in FIG. 12.

Let the spectral sensitivity at wave length λ of the R photoelectric conversion element shown in FIG. 8 be R(λ), the spectral sensitivity at wave length λ of the G photoelectric conversion element shown in FIG. 8 be G(λ), the spectral sensitivity at wave length λ of the B photoelectric conversion element shown in FIG. 8 be B(λ), the spectral sensitivity at wave length λ of the R second photoelectric conversion element shown in FIG. 8 be IR(λ), and the spectral sensitivity at wave length λ of the photoelectric conversion element having the characteristic represented by the Real curve shown in FIG. 12 be Real(λ). In this case, the coefficients r1, g1, b1, and ir1 are determined by the least squares method so that the value obtained by performing computation of the following expression (2) becomes as close as possible to Real(λ). The determined coefficient data is previously stored in a memory (not shown) of the endoscope.

$$r1\times R(\lambda)+g1\times G(\lambda)+b1\times B(\lambda)+ir1\times IR(\lambda) \quad (2)$$

FIG. 13 is a drawing to show the spectral sensitivity characteristic obtained by performing the computation of the expression (2) using the coefficients determined by the above-mentioned method. In FIG. 13, the vertical axis indicates the spectral sensitivity where 1 is used as a reference, and the horizontal axis indicates the wavelength of light. Curve I shown in FIG. 13 becomes the spectral sensitivity characteristic of a virtual photoelectric conversion element that can obtain high-contrast infrared image data obtained by performing the computation of the expression (1).

Figure 15:
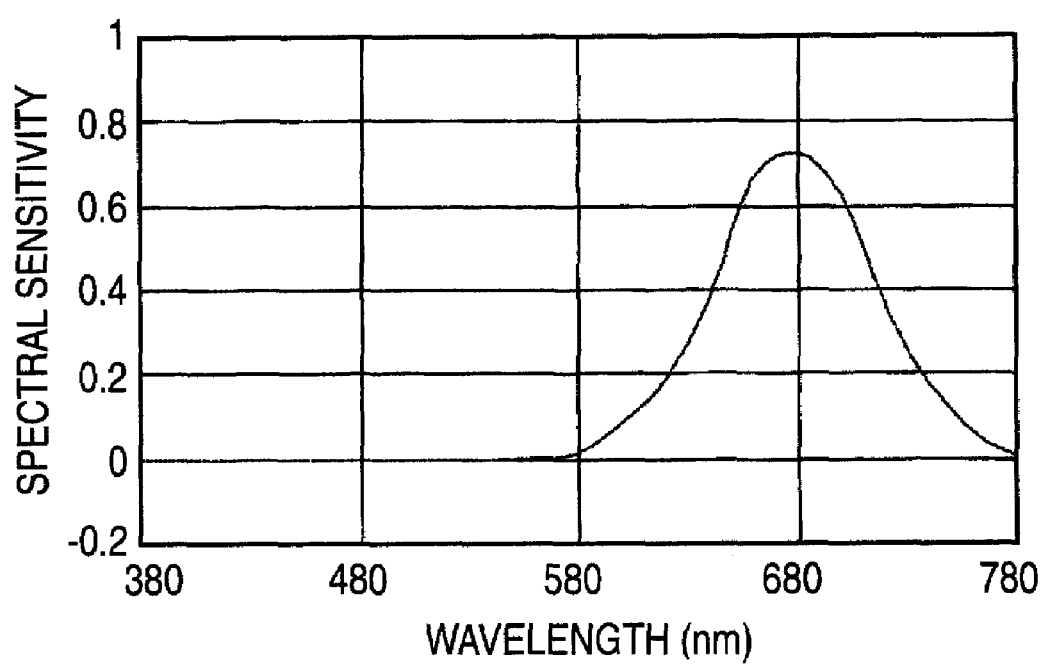
FIG. 15 is a drawing to show the spectral sensitivity characteristic of R second photoelectric conversion element shown in FIG. 8.

FIG. 14 is a drawing to show the detection sensitivities of oxygenated hemoglobin and reduced hemoglobin when light from hemoglobin is detected by the photoelectric conversion element having the spectral sensitivity characteristic shown in FIG. 13. In FIG. 14, the vertical axis indicates the spectral sensitivity where 1 is used as a reference, and the horizontal axis indicates the wavelength of light. FIG. 15 is a drawing to show the spectral sensitivity characteristic of the R second photoelectric conversion element shown in FIG. 8. In FIG. 15, the vertical axis indicates the spectral sensitivity where 1 is used as a reference, and the horizontal axis indicates the wavelength of light. FIG. 16 is a drawing to show the detection sensitivities of oxygenated hemoglobin and reduced hemoglobin when light from hemoglobin is detected by the R second photoelectric conversion element having the spectral sensitivity characteristic shown in FIG. 15. In FIG. 16, the vertical axis indicates the spectral sensitivity where 1 is used as reference, and the horizontal axis indicates the wavelength of light.

Comparing FIGS. 14 and 16, the contrast ratio of high-contrast infrared image data represented by a value resulting from dividing an area A surrounded by oxygenated hemoglobin waveform I(oxy) shown in FIG. 14 and the line with spectral sensitivity=0 by an area B surrounded by reduced hemoglobin waveform I(deoxy) and the line with spectral sensitivity=0 shown in FIG. 14 is 1.318, and the contrast ratio of high-contrast infrared image data represented by a value resulting from dividing an area C surrounded by oxygenated hemoglobin waveform I(oxy) shown in FIG. 16 and the line with spectral sensitivity=0 by an area D surrounded by reduced hemoglobin waveform I(deoxy) and the line with spectral sensitivity=0 shown in FIG. 16 is 1.166. It can be seen that the contrast of the infrared image data can be improved by performing the computation process represented by the expression (1).

Since the image pickup device for use in the endoscope according to the embodiment needs to output an IR signal, an infrared cut film as installed in a usual digital camera cannot be placed in front of the image pickup device. In the embodiment, a correction filter 52 for correcting the spectral sensitivity characteristic of the photoelectric conversion layer 9 is provided. Thus, each of the R, G, and B first photoelectric conversion elements has less infrared-region light sensitivity, but has some infrared-region light sensitivity. Consequently, it is concerned that color reproducibility of color image data may be deteriorated.

Figure 17:
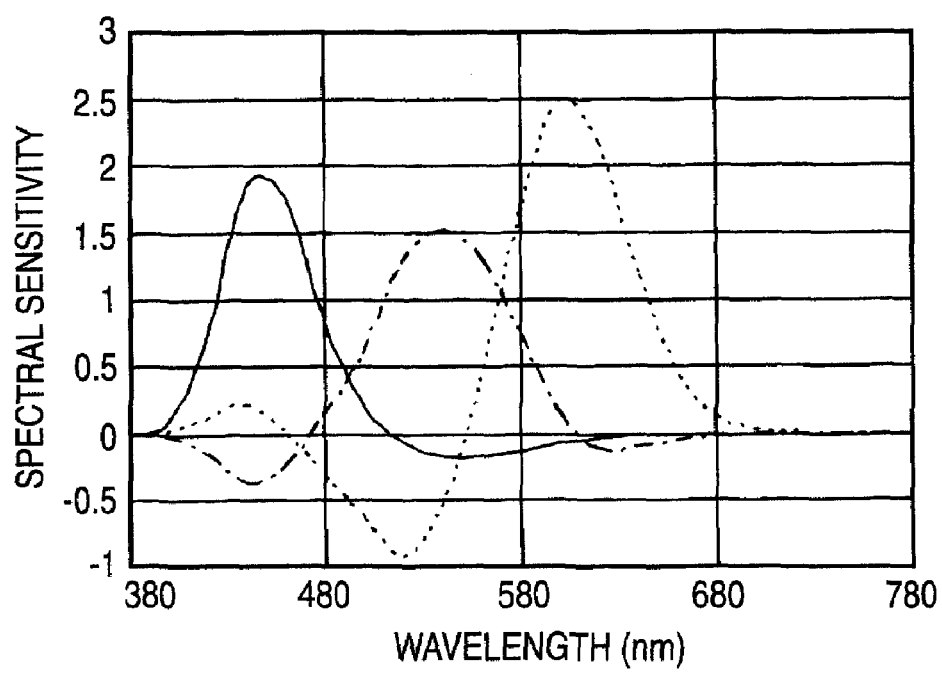
FIG. 17 is a drawing to show standard RGB ideal image pickup characteristic.

Then, the high-color-reproduction color image data generation section 56 performs a computation process of bringing the R signal obtained from the R first photoelectric conversion element to be close to a signal obtained from an r photoelectric conversion element having an ideal spectral sensitivity characteristic defined by the standard RGB ideal image pickup characteristic shown in FIG. 17, performs a computation process of bringing the G signal obtained from the G photoelectric conversion element to be close to a signal obtained from a g photoelectric conversion element having an ideal spectral sensitivity characteristic defined by the standard RGB ideal image pickup characteristic shown in FIG. 17, and performs a computation process of bringing the B signal obtained from the B photoelectric conversion element to be close to a signal obtained from a b photoelectric conversion element having an ideal spectral sensitivity characteristic defined by the standard RGB ideal image pickup characteristic shown in FIG. 17, to thereby generate high-color-reproduction color image data.

Specifically, the high-color-reproduction color image data generation section 56 performs computation represented by the following expression (3) to improve the color reproducibility of the color image data:

$$\begin{pmatrix} R_O(x, y) \\ G_O(x, y) \\ B_O(x, y) \end{pmatrix} = \begin{pmatrix} r2 & g2 & b2 & ir2 \\ r3 & g3 & b3 & ir3 \\ r4 & g4 & b4 & ir4 \end{pmatrix} \begin{pmatrix} R(x, y) \\ G(x, y) \\ B(x, y) \\ Ir(x, y) \end{pmatrix} \quad (3)$$

where Ro(x, y) denotes an R component of pixel data of high-color-reproduction color image data at coordinates (x, y), Go (x, y) denotes a G component of the pixel data of the high-color-reproduction color image data at the coordinates (x, y), Bo (x, y) denotes a B component of the pixel data of the high-color-reproduction color image data at the coordinates (x, y), R(x, y) denotes an R component of pixel data of the color image data at the coordinates (x, y), G(x, y) denotes a G component of the pixel data of the color image data at the coordinates (x, y), B(x, y) denotes a B component of the pixel data of the color image data at the coordinates (x, y), Ir(x, y) denotes an IR component of pixel data of the infrared image data at the coordinates (x, y), and r2, r3, r4, g2, g3, g4, b2, b3, b4, ir2, ir3, and ir4 denote coefficients which are determined based on the spectral sensitivity characteristic of the R first photoelectric conversion element, the spectral sensitivity characteristic of the G first photoelectric conversion element, the spectral sensitivity characteristic of the B first photoelectric conversion element, the spectral sensitivity characteristic of the R second photoelectric conversion element, and the standard RGB ideal image pickup characteristic shown in FIG. 17.

Let the spectral sensitivity at wave length λ of the R first photoelectric conversion element shown in FIG. 8 be R(λ), the spectral sensitivity at wave length λ of the G first photoelectric conversion element shown in FIG. 8 be G(λ), the spectral sensitivity at wave length λ of the B first photoelectric conversion element shown in FIG. 8 be B(λ), the spectral sensitivity at wave length λ of the R second photoelectric conversion element shown in FIG. 8 be IR(λ), and the spectral sensitivity at wave length λ of the r photoelectric conversion element shown in FIG. 17 is r(λ). In this case, the coefficients r2, g2, b2, and ir2 are determined by the least squares method so that a value obtained by the following expression (4) is as close as possible to r(λ). The determined coefficient data is previously stored in the memory (not shown) of the endoscope.

$$r2 \times R(\lambda) + g2 \times G(\lambda) + b2 \times B(\lambda) + ir2 \times IR(\lambda) \quad (4)$$

Let the spectral sensitivity at wave length λ of the g photoelectric conversion element shown in FIG. 17 be g(λ). In this case, the coefficients r3, g3, b3, and ir3 are determined by the least squares method so that a value obtained by the following expression (5) is as close as possible to g(λ). The determined coefficient data is previously stored in the memory (not shown) of the endoscope.

$$r3 \times R(\lambda) + g3 \times G(\lambda) + b3 \times B(\lambda) + ir3 \times IR(\lambda) \quad (5)$$

Let the spectral sensitivity at wave length λ of the b photoelectric conversion element shown in FIG. 17 be b(λ). In this case, the coefficients r4, g4, b4, and ir4 are determined by the least squares method so that a value obtained by the following expression (6) is as close as possible to b(λ). The determined coefficient data is previously stored in the memory (not shown) of the endoscope.

$$r4 \times R(\lambda) + g4 \times G(\lambda) + b4 \times B(\lambda) + ir4 \times IR(\lambda) \quad (6)$$

Figure 18:
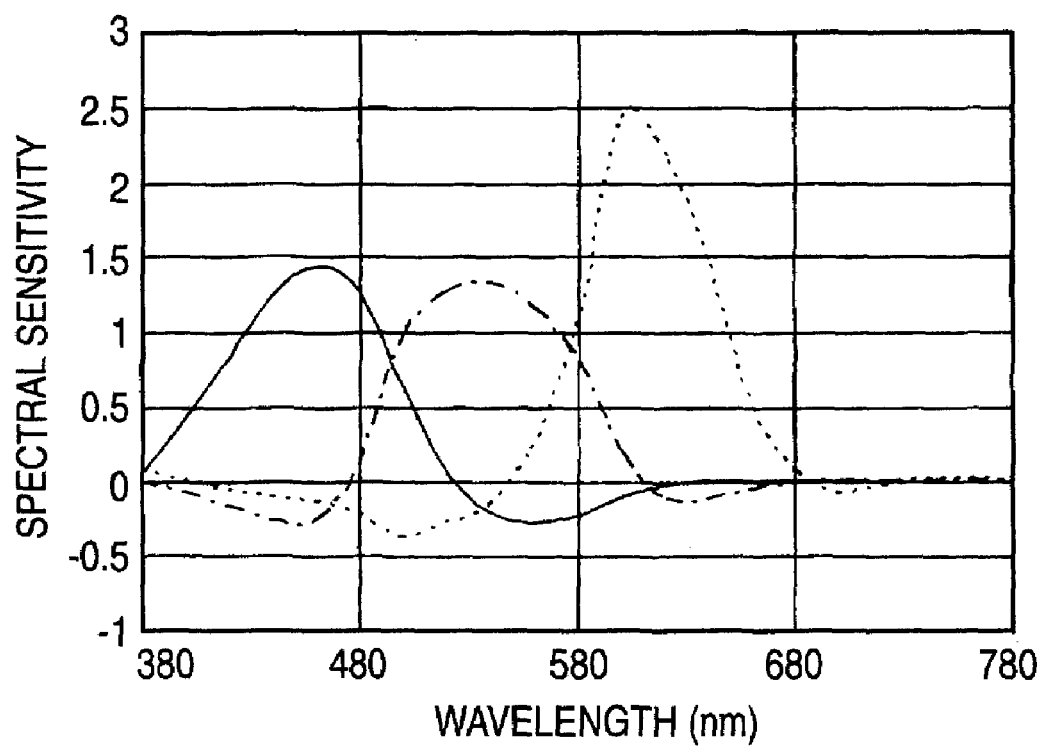
FIG. 18 is a drawing to show characteristics obtained by performing a process of bringing the characteristics of the R, G, and B first photoelectric conversion elements of the image pickup device shown in FIG. 1 to be close to the characteristics shown in FIG. 17.

FIG. 18 is a drawing to show the spectral sensitivity characteristics of the R, G, and B photoelectric conversion elements of the image pickup device 100 obtained as a result of performing the computations of the expressions (4) to (6) using the coefficients determined by the method described above. In FIG. 18, the vertical axis indicates the spectral sensitivity where 1 is used as a reference, and the horizontal axis indicates the wavelength. Curve R shown in FIG. 18 indicates the spectral sensitivity characteristic obtained as a result of bringing the spectral sensitivity characteristic of the R first photoelectric conversion element to be close to the ideal spectral sensitivity characteristic, curve G shown in FIG. 18 indicates the spectral sensitivity characteristic obtained as a result of bringing the spectral sensitivity characteristic of the G first photoelectric conversion element to be close to the ideal spectral sensitivity characteristic, and curve B shown in FIG. 18 indicates the spectral sensitivity characteristic obtained as a result of bringing the spectral sensitivity characteristic of the B first photoelectric conversion element to be close to the ideal spectral sensitivity characteristic.

As shown in FIG. 18, the infrared region sensitivity of wavelength 680 nm or more can be set almost to 0 or less. Thus, it can be seen that the color reproducibility of the color image data can be improved by performing the computation process represented by the expression (3).

The display control section 58 controls the display 59 to display an image based on the high-contrast infrared image data enhanced by the image enhancement section 57, controls the display 59 to display an image based on the high-color-reproduction color image data, and controls the display 59 to display an image into which the image based on the high-contrast infrared image data and the image based on the high-color-reproduction color image data are combined. For the high-contrast infrared image data, a signal level is represented in pseudo color to display an image or the signal level is converted into an oxygen absorption amount to display an image.

As described above, according to the endoscope of the embodiment, the computation process is performed using the color image data generated from the R, G, and B signals output from the image pickup device 100 and the infrared image data generated from the IRr signal output from the image pickup device 100. Thereby, high-color-reproduction color image data with the color reproducibility improved as compared with the color image data and high-contrast infrared image data with the contrast improved as compared with the infrared image data can be generated. Thus, the test accuracy of the endoscope can be improved than was previously possible.

When the image pickup device having the configuration described in the first embodiment is adopted as an image pickup device for use in the endoscope, high-color-reproduction color image data and high-contrast infrared image data can be obtained by a single image picking up process. Therefore, it is made possible to conduct test without worrying about a color shift, etc.

The endoscope of the embodiment eliminates the need for an infrared cut filter, so that it is made possible to miniaturize a part to be inserted into a human body and the endoscope cost can also be reduced.

In the description given above, the endoscope is provided with the correction filter 52, which may be omitted. If the correction filter 52 is omitted, the spectral sensitivity characteristic of the image pickup device 100 for use in the endoscope becomes as shown in FIG. 6 and the color reproducibility of the color image data is more deteriorated. Thus, the process performed by the high-color-reproduction color image data generation section 56 becomes more advantageous.

In the embodiment, the endoscope is provided with both the high-contrast infrared image data generation section 55 and the high-color-reproduction color image data generation section 56. However, the high-color-reproduction color image data generation section 56 may be omitted. If the high-color-reproduction color image data generation section 56 is omitted, preferably the correction filter 52 to cut the wavelength range of 780 nm or more is provided.

The high-color-reproduction color image data generation section 56 is installed not only in the endoscope, but also in an image pickup apparatus such as a digital camera that has an image pickup device capable of outputting an R component signal, a G component signal, a B component signal, and an IR component signal. Thereby, a sufficient effect can be produced. In this case, an infrared cut filter is not required for the image pickup apparatus, so that the image pickup apparatus can be miniaturized and the cost thereof can be reduced.

The functions of the infrared image data generation section 53, the color image data generation section 54, the high-contrast infrared image data generation section 55, the high-color-reproduction color image data generation section 56, and the image enhancement section 57 in the endoscope described above may be implemented as a computer such as a processing unit installed in the endoscope executes a program for causing the computer to function as these sections. The functions of these sections may also be implemented as an image pickup signal obtained from the image pickup device 100 is input into a personal computer, etc., as it is and the computer executes the above-mentioned program.

In the specification, the R wavelength range indicates the range of wavelengths about 550 nm to about 700 nm, the G wavelength range indicates the range of wavelengths about 450 nm to about 610 nm, the B wavelength range indicates the range of wavelengths about 380 nm to about 520 nm, the infrared region indicates the range of wavelengths about 680 nm to about 3000 nm, the Cy wavelength range indicates the range of wavelengths about 380 nm to about 610 nm, the Mg wavelength range indicates the range of wavelengths about 380 nm to about 500 nm and wavelengths about 600 nm to 700 nm, and the Ye wavelength range indicates the range of wavelengths about 470 nm to about 700 nm.

In the specification, the expression "to transmit light in one wavelength range" is used to mean transmitting about 60% or more of the light in such a wavelength range and "to absorb light in one wavelength range" is used to mean absorbing about 50% or more of the light in such a wavelength range.

What is claimed is:

1. An image processing apparatus for generating image data from an image pickup signal output from an image pickup device, the apparatus comprising:

a color image data generation unit that generates color image data from an image pickup signal of a red component, an image pickup signal of a green component, and an image pickup signal of a blue component which are output from the image pickup device;

an infrared image data generation unit that generates infrared image data from an image pickup signal of an infrared component output from the image pickup device; and a high-contrast infrared image data generation unit that generates high-contrast infrared image data using the color image data and the infrared image data, wherein: contrast of the high-contrast infrared image data is more enhanced than that of the infrared image data, wherein:

pixel data of the color image data includes red-component data, green-component data and blue-component data, pixel data of the infrared image data includes infrared-component data, the high-contrast infrared image data generation unit generates the high-contrast infrared image data using the following expression:

$$I(x,y) = r1 \times R(x,y) + g1 \times G(x,y) + b1 \times B(x,y) + ir1 \times IR(x,y)$$

where I(x, y) denotes pixel data of the high-contrast infrared image data at coordinates (x, y), R(x, y) denotes the red-component data of the pixel data at the coordinates (x, y), G(x, y) denotes the green-component data of the pixel data at the coordinates (x, y), B(x, y) denotes the blue-component data of the pixel data at the coordinates (x, y), and r1, g1, b1 and ir1 denote coefficients, and the coefficients r1, g1, b1, and ir1 are determined so that $r1 \times R(\lambda) + g1 \times G(\lambda) + b1 \times B(\lambda) + ir1 \times IR(\lambda)$ is as close as possible to Real($\lambda$), where R($\lambda$) denotes a spectral sensitivity of a red-component photoelectric conversion element of the photoelectric conversion elements that outputs the image pickup signal of the red component, G($\lambda$) denotes a spectral sensitivity of a green-component photoelectric conversion element of the photoelectric conversion elements that outputs the image pickup signal of the green component, B($\lambda$) denotes a spectral sensitivity of a blue-component photoelectric conversion element of the photoelectric conversion elements that outputs the image pickup signal of the blue component, IR($\lambda$) denotes a spectral sensitivity of an infrared-component photoelectric conversion element of the photoelectric conversion elements that outputs the image pickup signal of the infrared component, and Real ($\lambda$) denotes a spectral sensitivity with which a observation target substance used to grasp change in a human body can be picked up with the highest contrast.

2. The apparatus according to claim 1, wherein the observation target substance is hemoglobin.

3. The apparatus according to claim 1, further comprising:

a high-color-reproduction color image data generation unit that generates high-color-reproduction color image data using the color image data and the infrared image data, wherein:

the high-color-reproduction color image data has color reproducibility higher than the color image data.

4. The apparatus according to claim 3, wherein:
the high-color-reproduction color image data generation unit generates each pixel data of the high-color-reproduction color image data using the following expression:

$$\begin{pmatrix} R_O(x,y) \\ G_O(x,y) \\ B_O(x,y) \end{pmatrix} = \begin{pmatrix} r2 & g2 & b2 & ir2 \\ r3 & g3 & b3 & ir3 \\ r4 & g4 & b4 & ir4 \end{pmatrix} \begin{pmatrix} R(x,y) \\ G(x,y) \\ B(x,y) \\ Ir(x,y) \end{pmatrix}$$

where
$R_O(x, y)$ denotes red-component data of the pixel data of the high-color-reproduction color image data at coordinates (x, y),
$G_O(x, y)$ denotes green-component data of the pixel data of the high-color-reproduction color image data at the coordinates (x, y),
$B_O(x, y)$ denotes blue-component data of the pixel data of the high-color-reproduction color image data at the coordinates (x, y),
$R(x, y)$ denotes the red-component data of the pixel data of the color image data at the coordinates (x, y),
$G(x, y)$ denotes the green-component data of the pixel data of the color image data at the coordinates (x, y),
$B(x, y)$ denotes the blue-component data of the pixel data of the color image data at the coordinates (x, y),
$Ir(x, y)$ denotes the infrared-component data of the pixel data of the color image data at the coordinates (x, y), and
r2, r3, r4, g2, g3, g4, b2, b3, b4, ir2, ir3 and ir4 denote coefficients,
the coefficients r2, g2, b2, and ir2 are determined so that $r2 \times R(\lambda) + g2 \times G(\lambda) + b2 \times B(\lambda) + ir2 \times IR(\lambda)$ is as close as possible to $R_O(\lambda)$, where
$R(\lambda)$ denotes a spectral sensitivity of a red-component photoelectric conversion element of the photoelectric conversion elements that outputs the image pickup signal of the red component,
$G(\lambda)$ denotes a spectral sensitivity of a green-component photoelectric conversion element of the photoelectric conversion elements that outputs the image pickup signal of the green component,
$B(\lambda)$ denotes a spectral sensitivity of a blue-component photoelectric conversion element of the photoelectric conversion elements that outputs the image pickup signal of the blue component,
$IR(\lambda)$ denotes a spectral sensitivity of an infrared-component photoelectric conversion element of the photoelectric conversion elements that outputs the image pickup signal of the infrared component, and
$R_O(\lambda)$ denotes an ideal spectral sensitivity of a photoelectric conversion element that outputs an image pickup signal of the red component,
the coefficients r3, g3, b3, and ir3 are determined so that $r3 \times R(\lambda) + g3 \times G(\lambda) + b3 \times B(\lambda) + ir3 \times IR(\lambda)$ is as close as possible to $G_O(\lambda)$, where $G_O(\lambda)$ denotes an ideal spectral sensitivity of a photoelectric conversion element that outputs an image pickup signal of the green component, and
the coefficients r4, g4, b4, and ir4 are determined so that $r4 \times R(\lambda) + g4 \times G(\lambda) + b4 \times B(\lambda) + ir4 \times IR(\lambda)$ is as close as possible to $B_O(\lambda)$, where $G_O(\lambda)$ denotes an ideal spectral sensitivity of a photoelectric conversion element that outputs an image pickup signal of the blue component.

5. The apparatus according to claim 1, wherein the image pickup device comprises:
a large number of first photoelectric conversion elements arranged on a first plane in a semiconductor substrate;
second photoelectric conversion elements formed on a second plane, which is located above the first photoelectric conversion elements, the second photoelectric conversion elements that correspond to a part of the large number of first photoelectric conversion elements, the second photoelectric conversion elements comprising:
first electrodes formed above the first photoelectric conversion elements,
a photoelectric conversion layer formed on the first electrodes, and
a second electrode formed on the photoelectric conversion layer;
a color filter layer formed above the first photoelectric conversion elements, the color filter layer that transmits light in a wavelength range different from a wavelength range of light that the photoelectric conversion layer absorbs; and
a signal reading portion that reads (i) signals that correspond to charges generated in the second photoelectric conversion elements and (ii) signals that correspond to charges generated in the first photoelectric conversion elements, wherein:
the color filter layer comprises a large number of color filters that correspond to the large number of photoelectric conversion elements, respectively,
the large number of color filters are classified into three types of color filters of those for transmitting light in a red wavelength range, those for transmitting light in a green wavelength range, and those for transmitting light in a blue wavelength range,
of the three types of color filters, at least the color filters for transmitting light in the red wavelength range also transmit infrared region light,
the photoelectric conversion layer absorbs the infrared region light to generate charges in response thereto, and transmits any other light than the infrared region light, and
the part of the large number of first photoelectric conversion elements are the first photoelectric conversion elements corresponding to the color filters for transmitting light in the red wavelength range.

6. The apparatus according to claim 5, wherein the color filter layer is formed above the second photoelectric conversion elements.

7. The apparatus according to claim 6, wherein:
the photoelectric conversion layer contains an organic material, and the image pickup device further comprises a protective layer that protects the second photoelectric conversion elements, the protective layer formed by an atomic layer chemical vapor deposition (ALCVD) method between the first photoelectric conversion elements and the color filter layer.

8. The apparatus according to claim 7, wherein the protective layer contains an inorganic material.

9. The apparatus according to claim 8, wherein the protective layer has a two-layer structure comprising an inorganic layer made of an inorganic material and an organic layer made of an organic polymer.

10. The apparatus according to claim 5, wherein the image pickup device further comprises a microlens that collects light in each of the large number of first photoelectric conversion elements.

11. An endoscope comprising:
an image processing apparatus; and
the image processing apparatus according to claim 1.

12. A non-transitory computer readable medium storing a program for causing a computer to execute a process for image processing, the image processing comprising:
generating color image data from an image pickup signal of a red component, an image pickup signal of a green component, and an image pickup signal of a blue component which are output from an image pickup device;
generating infrared image data from an image pickup signal of an infrared component output from the image pickup device; and
generating high-contrast infrared image data using the color image data and the infrared image data, wherein: contrast of the high-contrast infrared image data is more enhanced than that of the infrared image data, wherein:

$$I(x,y) = r1 \times R(x,y) + g1 \times G(x,y) + b1 \times B(x,y) + ir1 \times IR(x,y)$$

where I(x, y) denotes pixel data of the high-contrast infrared image data at coordinates
R(x, y) denotes the red-component data of the pixel data at the coordinates (x, y),
G(x, y) denotes the green-component data of the pixel data at the coordinates (x, y),
B(x, y) denotes the blue-component data of the pixel data at the coordinates (x, y), and
r1, g1, b1 and ir1 denote coefficients, and
the coefficients r1, g1, b1, and ir1 are determined so that $r1 \times R(\lambda) + g1 \times G(\lambda) + b1 \times B(\lambda) + ir1 \times IR(\lambda)$ is as close as possible to Real ($\lambda$), where
R($\lambda$) denotes a spectral sensitivity of a red-component photoelectric conversion element of the photoelectric conversion elements that outputs the image pickup signal of the red component,
G($\lambda$) denotes a spectral sensitivity of a green-component photoelectric conversion element of the photoelectric conversion elements that outputs the image pickup signal of the green component,
B($\lambda$) denotes a spectral sensitivity of a blue-component photoelectric conversion element of the photoelectric conversion elements that outputs the image pickup signal of the blue component,
IR($\lambda$) denotes a spectral sensitivity of an infrared-component photoelectric conversion element of the photoelectric conversion elements that outputs the image pickup signal of the infrared component, and
Real ($\lambda$) denotes a spectral sensitivity with which a observation target substance used to grasp change in a human body can be picked up with the highest contrast.

13. An image processing apparatus for generating image data from an image pickup signal output from an image pickup device, the apparatus comprising:
a color image data generation unit that generates color image data from an image pickup signal of a red component, an image pickup signal of a green component, and an image pickup signal of a blue component which are output from the image pickup device;
an infrared image data generation unit that generates infrared image data from an image pickup signal of an infrared component output from the image pickup device; and
a high-color-reproduction color image data generation unit that generates high-color-reproduction color image data using the color image data and the infrared image data, wherein:
the high-color-reproduction color image data has color reproducibility higher than the color image data, wherein:
the high-color-reproduction color image data generation unit generates each pixel data of the high-color-reproduction color image data using the following expression:

$$\begin{pmatrix} R_o(x,y) \\ G_o(x,y) \\ B_o(x,y) \end{pmatrix} = \begin{pmatrix} r2 & g2 & b2 & ir2 \\ r3 & g3 & b3 & ir3 \\ r4 & g4 & b4 & ir4 \end{pmatrix} \begin{pmatrix} R(x,y) \\ G(x,y) \\ B(x,y) \\ Ir(x,y) \end{pmatrix}$$

where Ro(x, y) denotes red-component data of the pixel data of the high-color-reproduction color image data at coordinates (x, y),
Go(x, y) denotes green-component data of the pixel data of the high-color-reproduction color image data at the coordinates (x, y),
Bo(x, y) denotes blue-component data of the pixel data of the high-color-reproduction color image data at the coordinates (x, y),
R(x, y) denotes the red-component data of the pixel data of the color image data at the coordinates (x, y),
G(x, y) denotes the green-component data of the pixel data of the color image data at the coordinates (x, y),
B(x, y) denotes the blue-component data of the pixel data of the color image data at the coordinates (x, y),
Ir(x, y) denotes the infrared-component data of the pixel data of the color image data at the coordinates (x, y), and
r2, r3, r4, g2, g3, g4, b2, b3, b4, ir2, ir3 and ir4 denote coefficients,
the coefficients r2, g2, b2, and ir2 are determined so that $r2 \times R(\lambda) + g2 \times G(\lambda) + b2 \times B(\lambda) + ir2 \times IR(\lambda))$ is as close as possible to Ro($\lambda$), where
R($\lambda$) denotes a spectral sensitivity of a red-component photoelectric conversion element of the photoelectric conversion elements that outputs the image pickup signal of the red component,
G($\lambda$) denotes a spectral sensitivity of a green-component photoelectric conversion element of the photoelectric conversion elements that outputs the image pickup signal of the green component,
B($\lambda$) denotes a spectral sensitivity of a blue-component photoelectric conversion element of the photoelectric conversion elements that outputs the image pickup signal of the blue component,
IR($\lambda$) denotes a spectral sensitivity of an infrared-component photoelectric conversion element of the photoelectric conversion elements that outputs the image pickup signal of the infrared component, and
Ro($\lambda$) denotes an ideal spectral sensitivity of a photoelectric conversion element that outputs an image pickup signal of the red component
the coefficients r3, g3, b3, and ir3 are determined so that $r3 \times R(\lambda) + g3 \times G(\lambda) + b3 \times B(\lambda) + ir3 \times IR(\lambda)$ is as close as possible to Go($\lambda$), where
Go($\lambda$) denotes an ideal spectral sensitivity of a photoelectric conversion element that outputs an image pickup signal of the green component, and
the coefficients r4, g4, b4, and ir4 are determined so that $r4 \times R(\lambda) + g4 \times G(\lambda) + b4 \times B(\lambda) + ir4 \times IR(\lambda)$ is as close as possible to Bo($\lambda$), where Go(λ) denotes an ideal spectral sensitivity of a photoelectric conversion element that outputs an image pickup signal of the blue component.

14. The apparatus according to claim 13, wherein the image pickup device comprises:
a large number of first photoelectric conversion elements arranged on a first plane in a semiconductor substrate;
second photoelectric conversion elements formed on a second plane, which is located above the first photoelectric conversion elements, the second photoelectric conversion elements that correspond to a part of the large number of first photoelectric conversion elements, the photoelectric conversion elements comprising:
first electrodes formed above the first photoelectric conversion elements,
a photoelectric conversion layer formed on the first electrodes, and
a second electrode formed on the photoelectric conversion layer;
a color filter layer formed above the first photoelectric conversion elements, the color filter layer that transmits light in a wavelength range different from a wavelength range of light that the photoelectric conversion layer absorbs; and
a signal reading portion that reads (i) signals that correspond to charges generated in the second photoelectric conversion elements and (ii) signals that correspond to charges generated in the first photoelectric conversion elements, wherein:
the color filter layer comprises a large number of color filters that correspond to the large number of photoelectric conversion elements, respectively,
the large number of color filters are classified into three types of color filters of those for transmitting light in a red wavelength range, those for transmitting light in a green wavelength range, and those for transmitting light in a blue wavelength range,
of the three types of color filters, at least the color filters for transmitting light in the red wavelength range also transmit infrared region light,
the photoelectric conversion layer absorbs the infrared region light to generate charges in response thereto, and transmits any other light than the infrared region light, and
the part of the large number of first photoelectric conversion elements are the first photoelectric conversion elements corresponding to the color filters for transmitting light in the red wavelength range.

15. The apparatus according to claim 14, wherein the color filter layer is formed above the second photoelectric conversion elements.

16. The apparatus according to claim 15, wherein:
the photoelectric conversion layer contains an organic material, and
the image pickup device further comprises a protective layer that protects the second photoelectric conversion elements, the protective layer formed by an atomic layer chemical vapor deposition (ALCVD) method between the first photoelectric conversion elements and the color filter layer.

17. The apparatus according to claim 16, wherein the protective layer contains an inorganic material.

18. The apparatus according to claim 17, wherein the protective layer has a two-layer structure comprising an inorganic layer made of an inorganic material and an organic layer made of an organic polymer.

19. The apparatus according to claim 14, wherein the image pickup device further comprises a microlens that collects light in each of the large number of first photoelectric conversion elements.

20. An endoscope comprising:
an image processing apparatus; and
the image processing apparatus according to claim 13.

21. A non-transitory computer readable medium storing a program for causing a computer to execute a process for image processing, the image processing comprising:
generating color image data from an image pickup signal of a red component, an image pickup signal of a green component, and an image pickup signal of a blue component which are output from an image pickup device;
generating infrared image data from an image pickup signal of an infrared component output from the image pickup device; and
generating high-color-reproduction color image data using the color image data and the infrared image data, wherein:
the high-color-reproduction color image data has color reproducibility higher than the color image data,
wherein:

$$I(x,y)=r1\times R(x,y)+g1\times G(x,y)+b1\times B(x,y)+ir1\times IR(x,y)$$

where I(x, y) denotes pixel data of the high-contrast infrared image data at coordinates (x, y),
R(x, y) denotes the red-component data of the pixel data at the coordinates (x, y),
G(x, y) denotes the green-component data of the pixel data at the coordinates (x, y),
B(x, y) denotes the blue-component data of the pixel data at the coordinates (x, y), and
r1, g1, b1 and ir1 denote coefficients, and
the coefficients r1, g1, b1, and ir1 are determined so that $r1\times R(\lambda)+g1\times G(\lambda)+b1\times B(\lambda)+ir1\times IR(\lambda)$ is as close as possible to Real (λ), where
R(λ) denotes a spectral sensitivity of a red-component photoelectric conversion element of the photoelectric conversion elements that outputs the image pickup signal of the red component,
G(λ) denotes a spectral sensitivity of a green-component photoelectric conversion element of the photoelectric conversion elements that outputs the image pickup signal of the green component,
B(λ) denotes a spectral sensitivity of a blue-component photoelectric conversion element of the photoelectric conversion elements that outputs the image pickup signal of the blue component,
IR(λ) denotes a spectral sensitivity of an infrared-component photoelectric conversion element of the photoelectric conversion elements that outputs the image pickup signal of the infrared component, and
Real (λ) denotes a spectral sensitivity with which a observation target substance used to grasp change in a human body can be picked up with the highest contrast.

* * * * *